(12) United States Patent
Tsukahara et al.

(10) Patent No.: US 10,805,574 B2
(45) Date of Patent: Oct. 13, 2020

(54) INFORMATION PROCESSING DEVICE, INFORMATION PROCESSING METHOD, AND PROGRAM FOR DECREASING REDUCTION OF VISIBILITY

(71) Applicant: SONY CORPORATION, Tokyo (JP)

(72) Inventors: Tsubasa Tsukahara, Tokyo (JP); Jun Kimura, Kanagawa (JP); Katsuya Hyodo, Kanagawa (JP); Daisuke Nakata, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/762,896

(22) PCT Filed: Sep. 16, 2016

(86) PCT No.: PCT/JP2016/077393
§ 371 (c)(1),
(2) Date: Mar. 23, 2018

(87) PCT Pub. No.: WO2017/057037
PCT Pub. Date: Apr. 6, 2017

(65) Prior Publication Data
US 2018/0234661 A1 Aug. 16, 2018

(30) Foreign Application Priority Data
Sep. 30, 2015 (JP) ................ 2015-193420

(51) Int. Cl.
*A61B 5/00* (2006.01)
*A61B 5/11* (2006.01)
(Continued)

(52) U.S. Cl.
CPC ............ *H04N 7/007* (2013.01); *A61B 5/1118* (2013.01); *A61B 5/6803* (2013.01);
(Continued)

(58) Field of Classification Search
CPC .......... H04N 5/64; H04N 7/007; G02B 27/01; G02B 2027/0178; G06F 3/01;
(Continued)

(56) References Cited

U.S. PATENT DOCUMENTS 9,367,668 B2 * 6/2016 Flynt .................... G06F 19/3481
10,134,368 B2 * 11/2018 O'Neill .................... G09G 5/30
(Continued)

*Primary Examiner* — Jacinta M Crawford
(74) *Attorney, Agent, or Firm* — Paratus Law Group, PLLC

(57) ABSTRACT

There is provided an information processing device, an information processing method, and a program that make it possible to decrease reduction in a recognition rate corresponding to the amount of exercise of a user wearing a wearable device. Acceleration information is acquired as exercise state information, and movement speed is calculated. If the movement speed exceeds certain speed, a plurality of pieces of information is displayed in a time-division manner for a certain amount of information each with which amount a recognition rate is not decreased, whereby a plurality of pieces of information is displayed while reduction in the recognition rate is controlled. The present technology can be applied to a wearable device.

19 Claims, 33 Drawing Sheets

(51) Int. Cl.
*G02B 27/01* (2006.01)
*H04N 7/00* (2011.01)
*H04N 5/64* (2006.01)
*G06F 3/0487* (2013.01)
*G06F 3/01* (2006.01)
*G06F 3/0481* (2013.01)
*G06K 9/00* (2006.01)
*G06T 19/00* (2011.01)
*A61B 5/024* (2006.01)
*A61B 5/01* (2006.01)
*A61B 5/0476* (2006.01)
*A61B 5/0488* (2006.01)

(52) U.S. Cl.
CPC ............ *A61B 5/7445* (2013.01); *G02B 27/01* (2013.01); *G06F 3/011* (2013.01); *G06F 3/0481* (2013.01); *G06F 3/0487* (2013.01); *G06K 9/00671* (2013.01); *G06T 19/006* (2013.01); *H04N 5/64* (2013.01); *A61B 5/01* (2013.01); *A61B 5/02438* (2013.01); *A61B 5/0476* (2013.01); *A61B 5/0488* (2013.01); *A61B 5/1113* (2013.01); *A61B 5/4266* (2013.01); *G02B 2027/0178* (2013.01)

(58) Field of Classification Search
CPC . G06F 3/0487; G06K 9/00671; G06T 19/006; A61B 5/01; A61B 5/02438; A61B 5/0476; A61B 5/0488; A61B 5/1113; A61B 5/1118; A61B 5/4266; A61B 5/6803; A61B 5/7445
USPC .......................................................... 345/7, 8
See application file for complete search history.

(56) References Cited

U.S. PATENT DOCUMENTS

| | | | |
|---|---|---|---|
| 2009/0100364 A1* | 4/2009 | Kinoshita | A61B 5/00 715/765 |
| 2011/0050707 A1* | 3/2011 | Kim | A63B 22/00 345/467 |
| 2012/0295764 A1* | 11/2012 | Brammer | A63B 24/0087 482/9 |
| 2013/0225370 A1* | 8/2013 | Flynt | A63B 24/0087 482/4 |
| 2013/0282157 A1* | 10/2013 | Shin | A63B 24/0062 700/91 |
| 2014/0081156 A1* | 3/2014 | Ohsawa | A61B 5/1123 600/483 |
| 2015/0253571 A1* | 9/2015 | Chen | G02B 27/017 345/8 |
| 2015/0331598 A1* | 11/2015 | Kang | G06F 3/014 715/765 |

* cited by examiner

[Fig. 1]
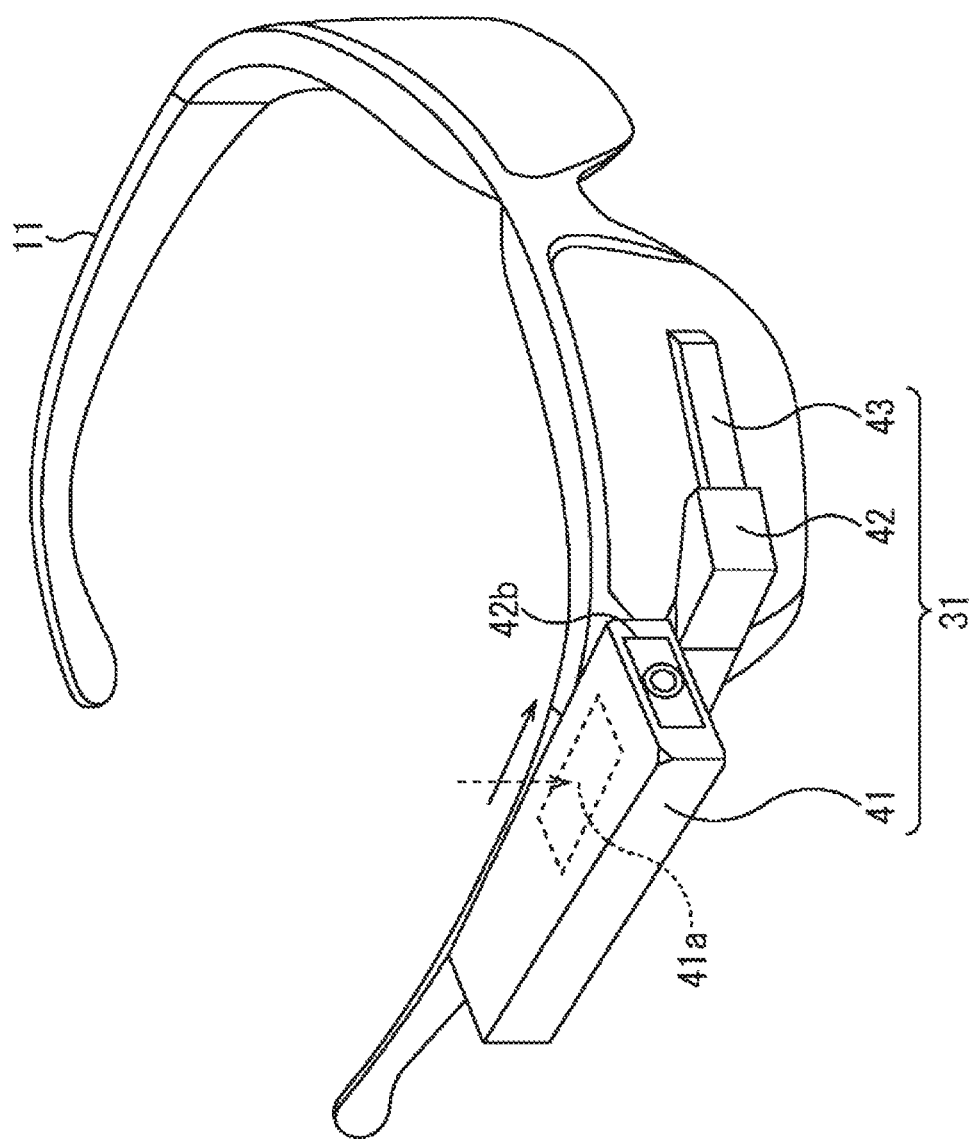

[Fig. 2]
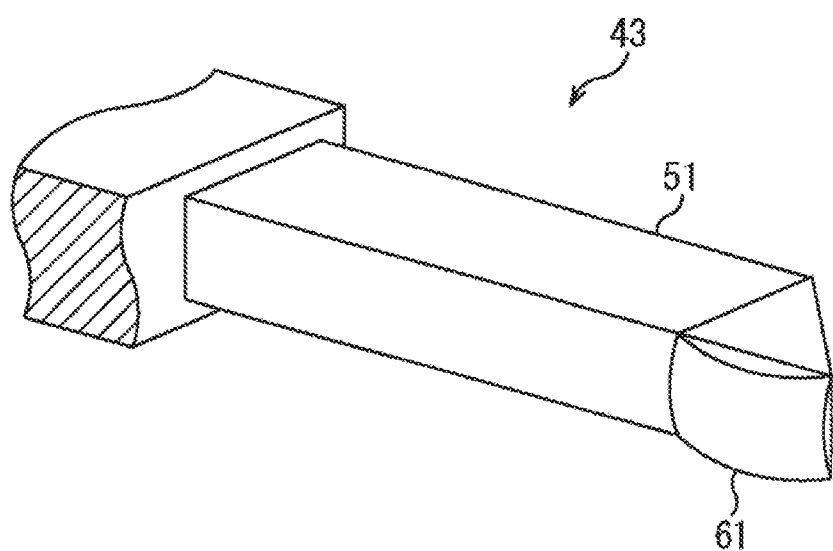

[Fig. 3]
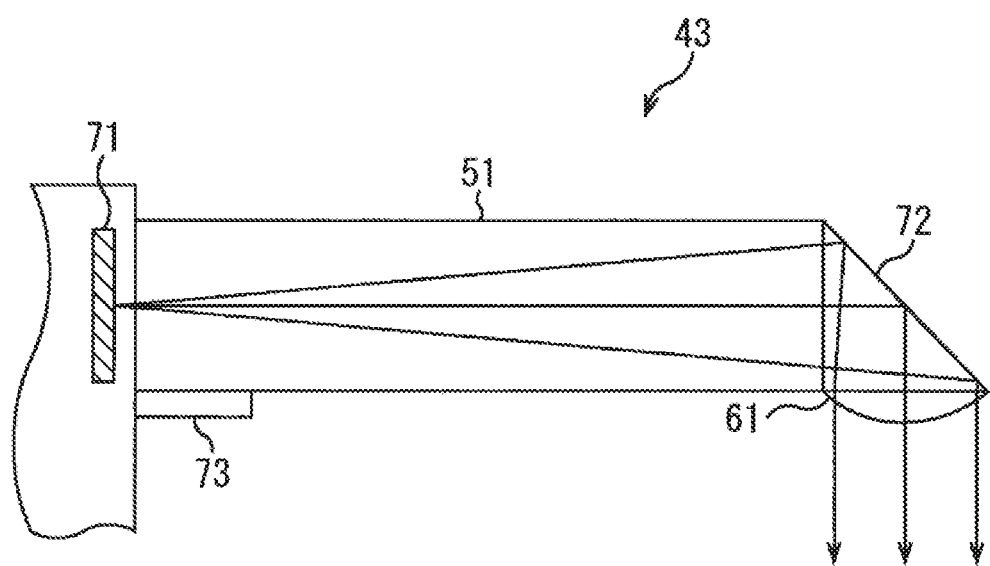

[Fig. 4]
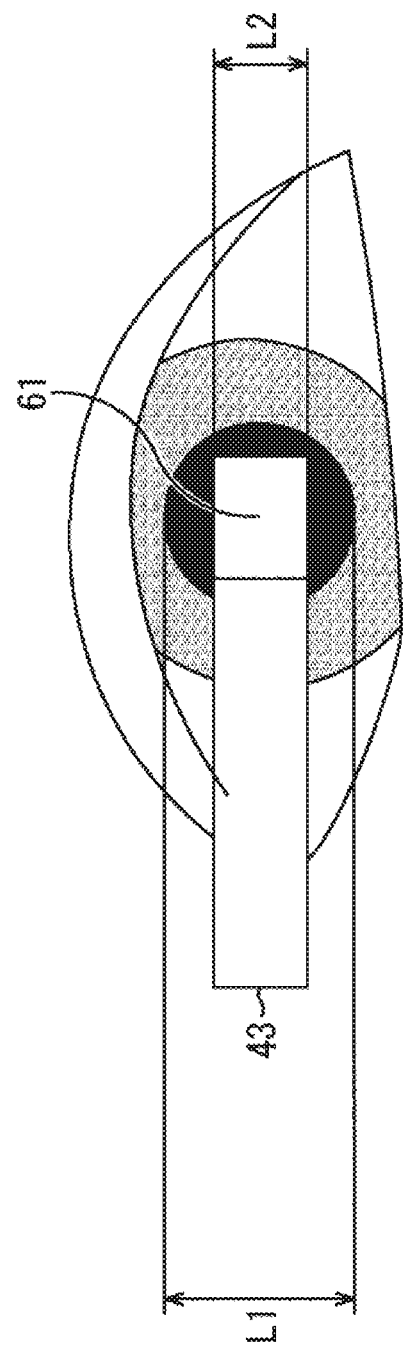

[Fig. 5]
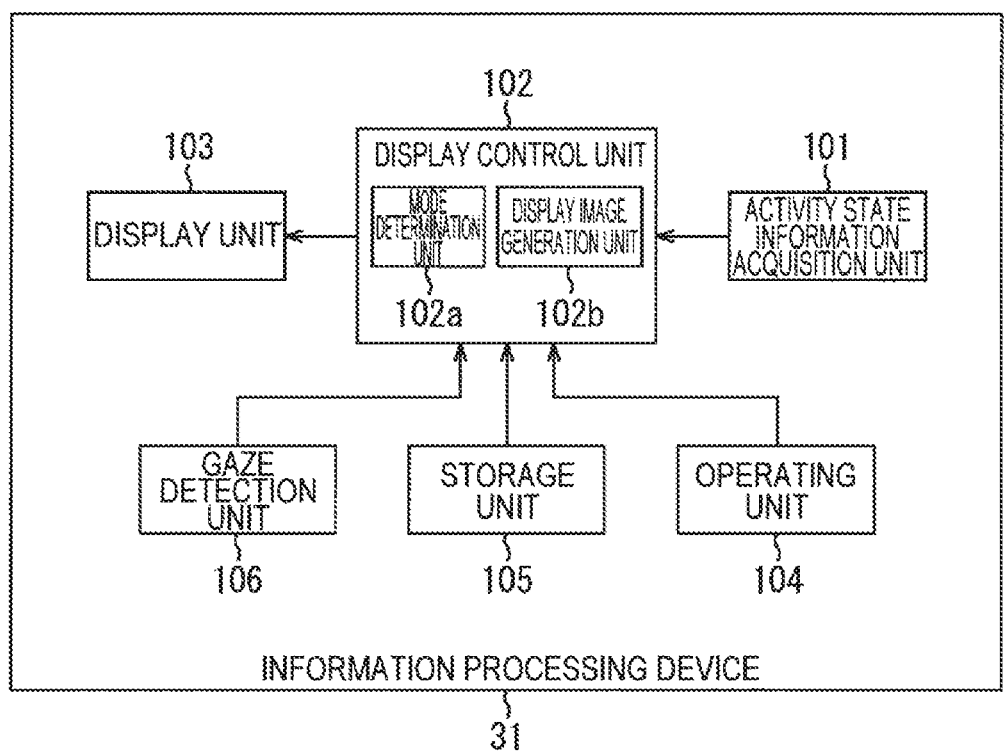

[Fig. 6]
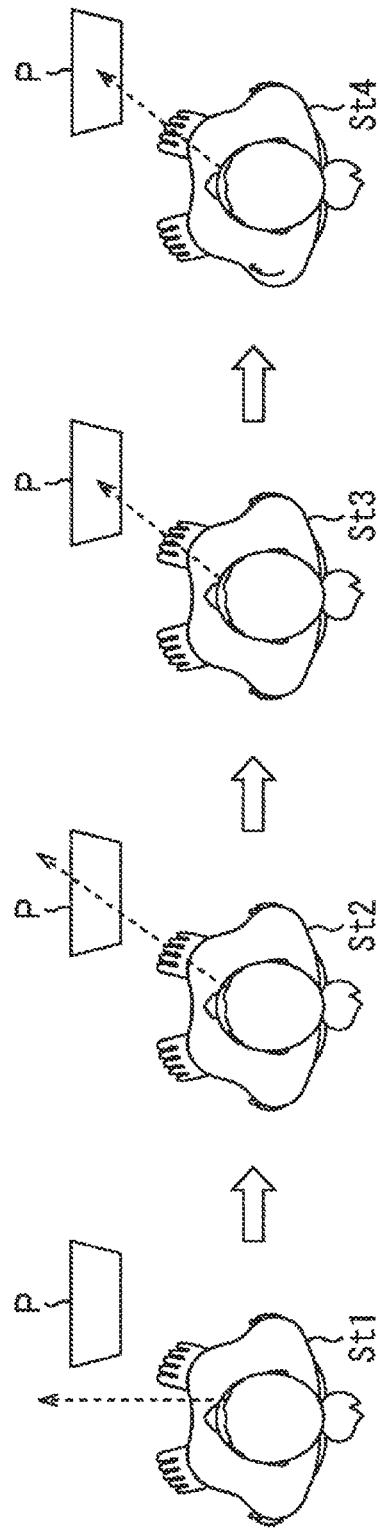

[Fig. 7]
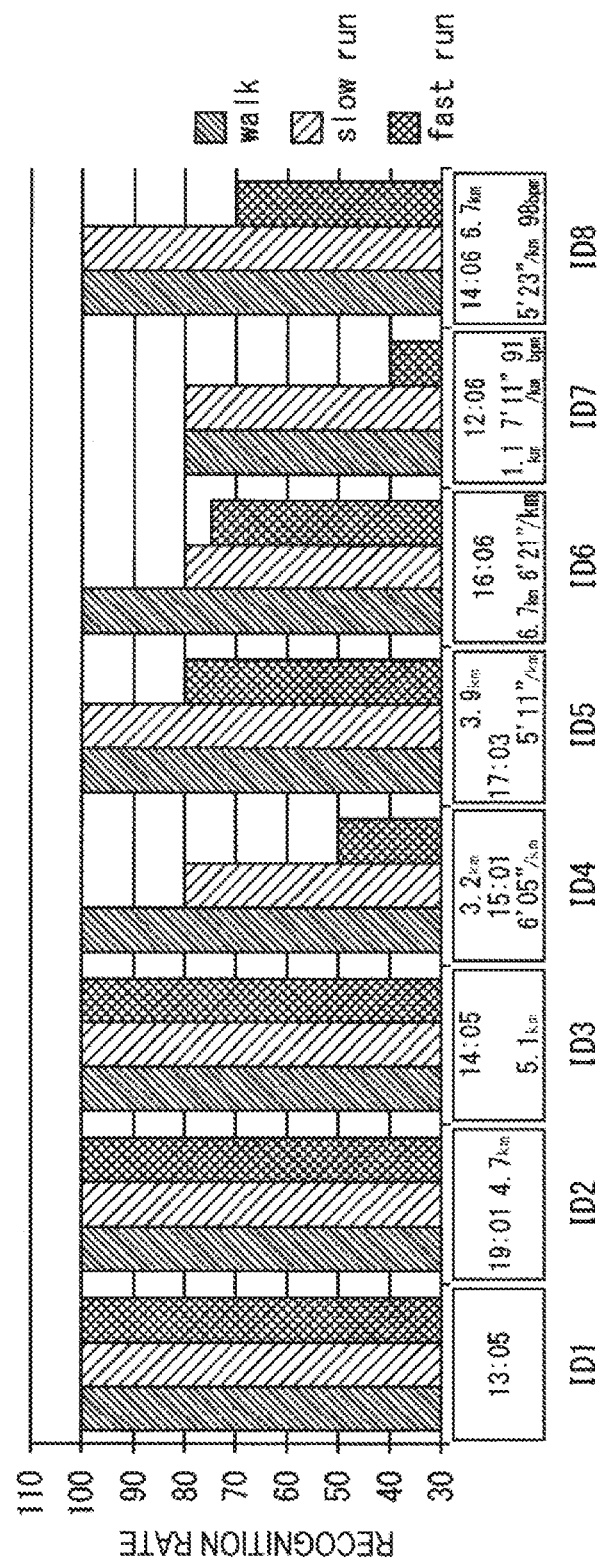

[Fig. 8]
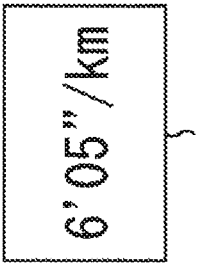
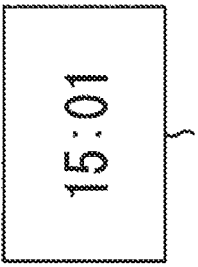
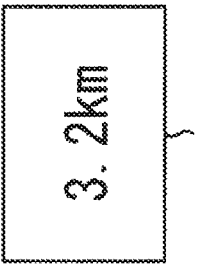
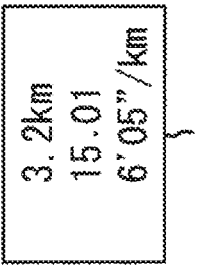

[Fig. 9]
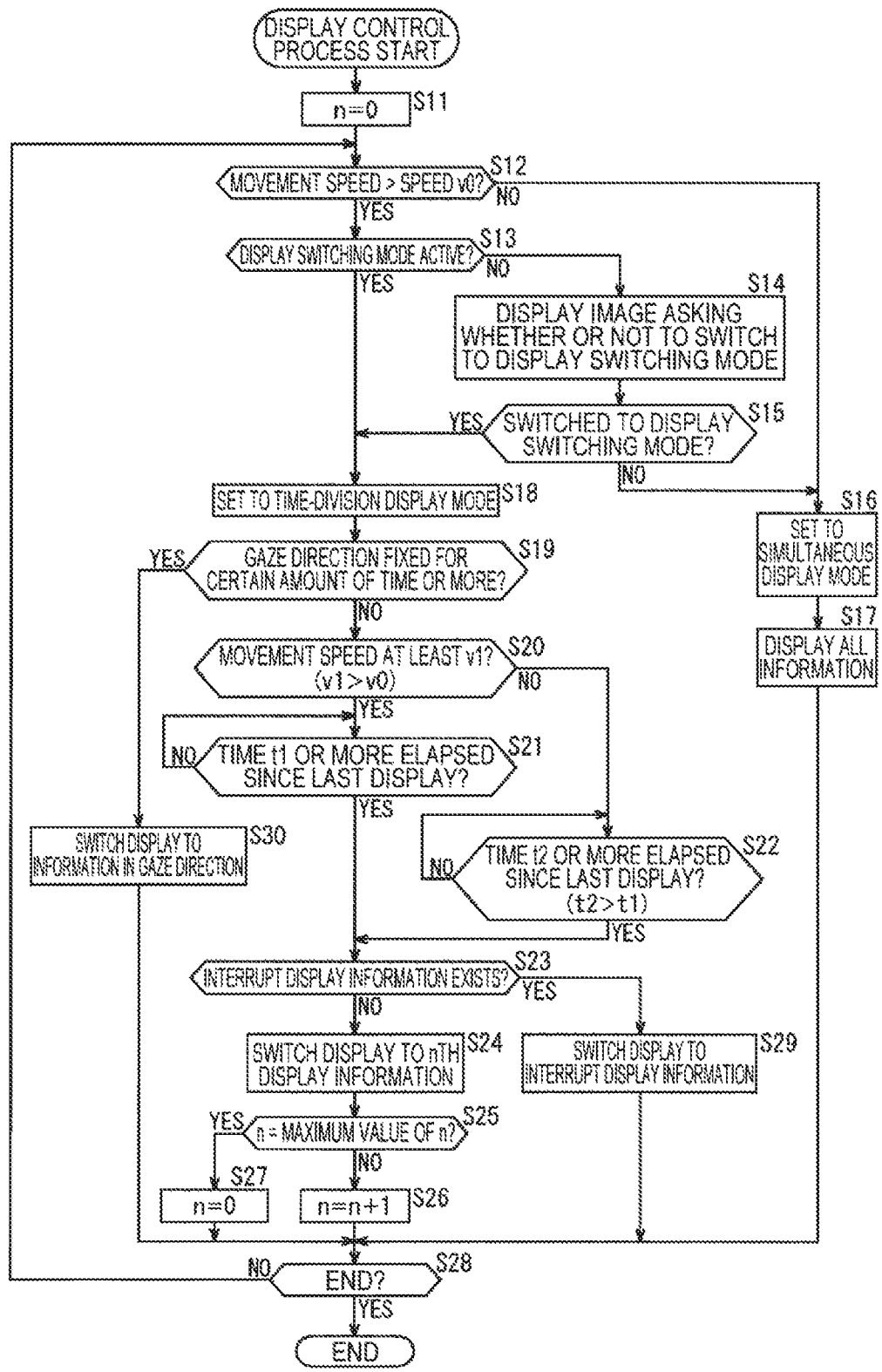

[Fig. 10]
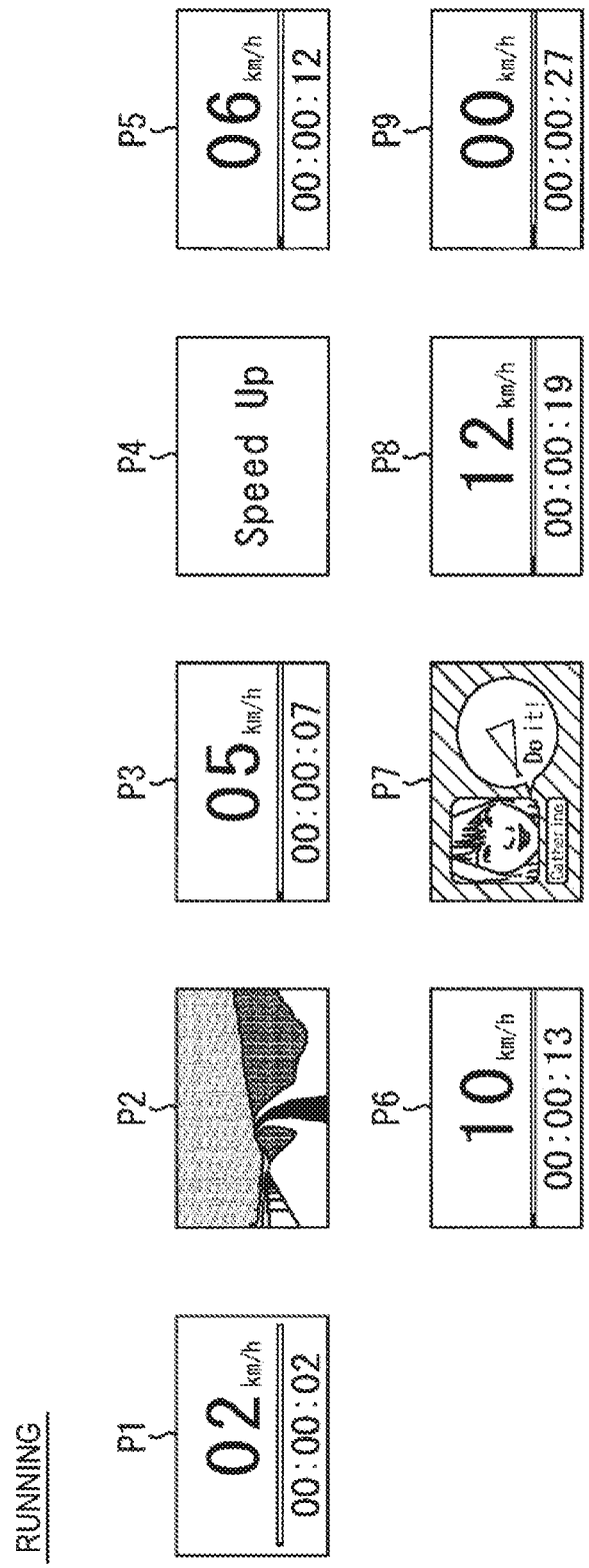

[Fig. 11]
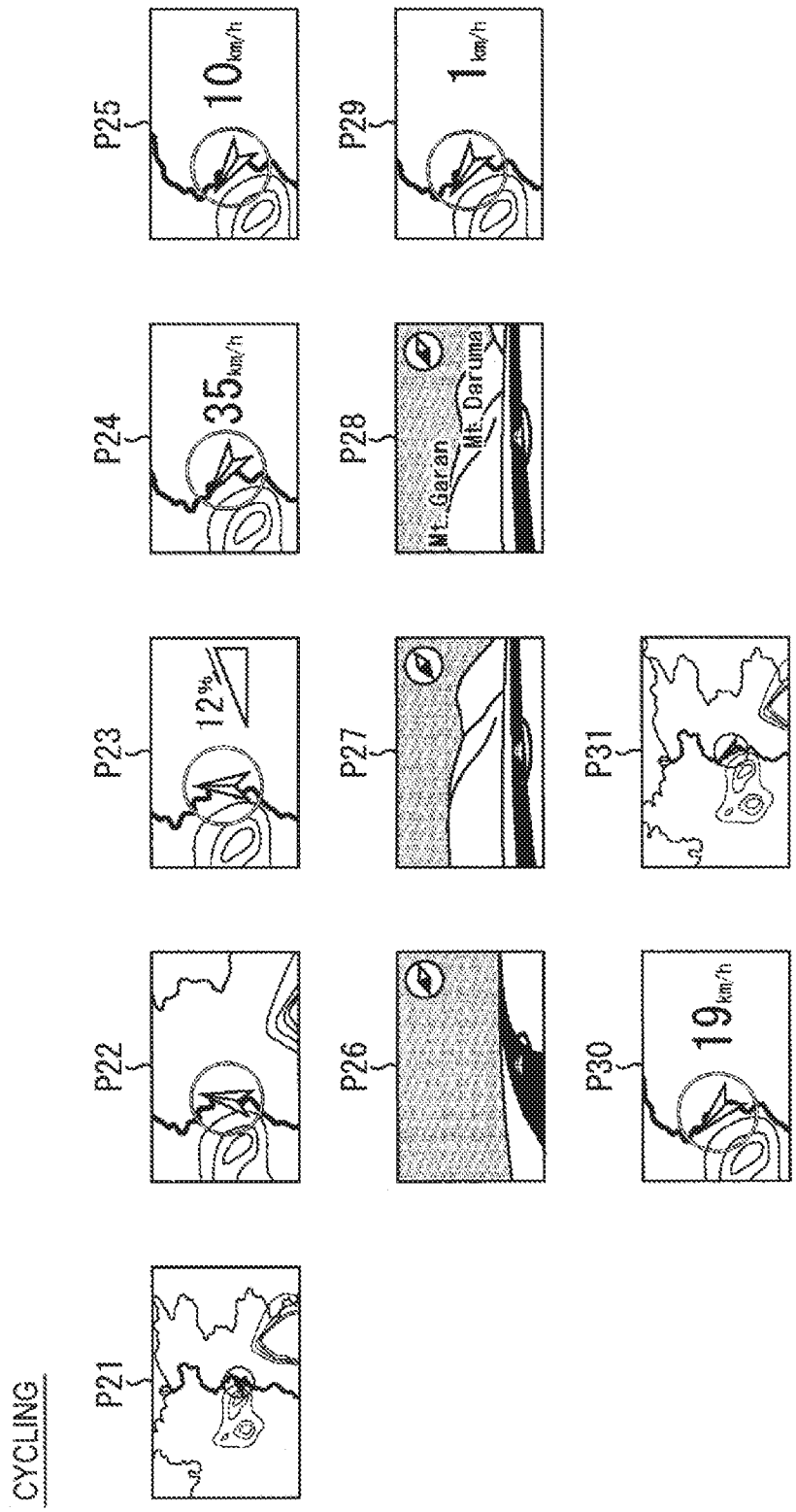

[Fig. 12]
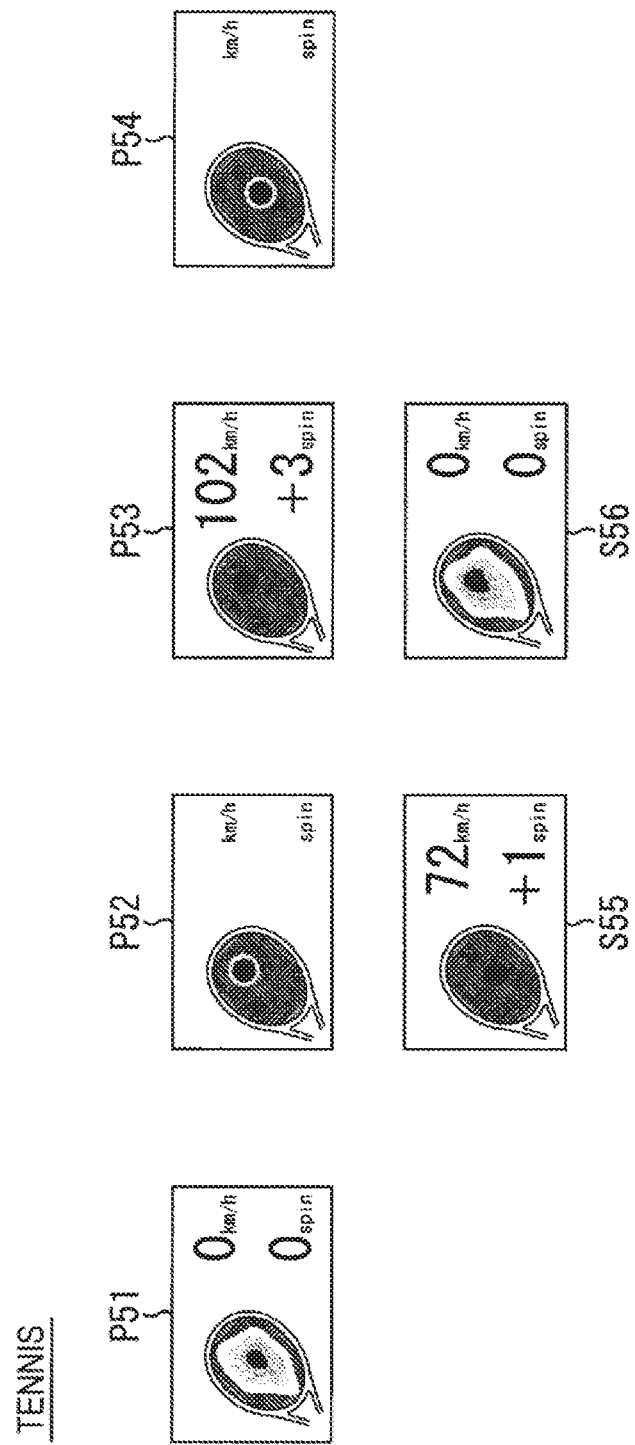

[Fig. 13]
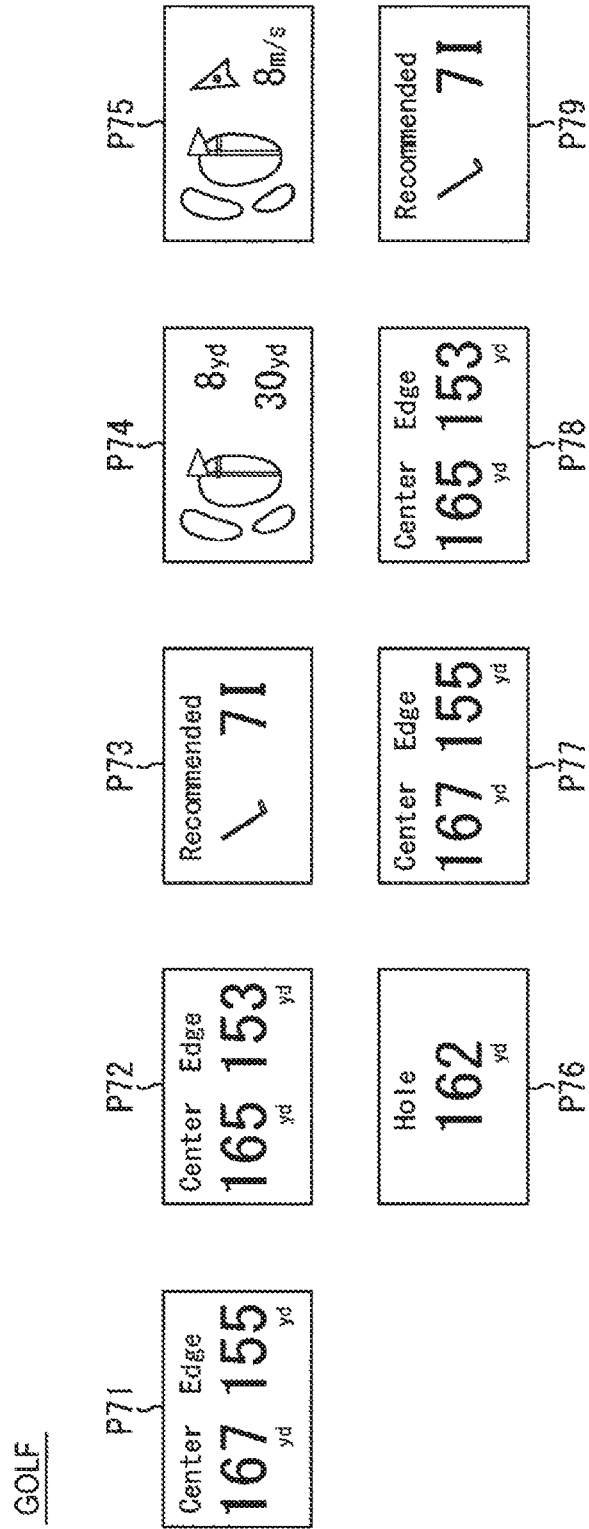

[Fig. 14]
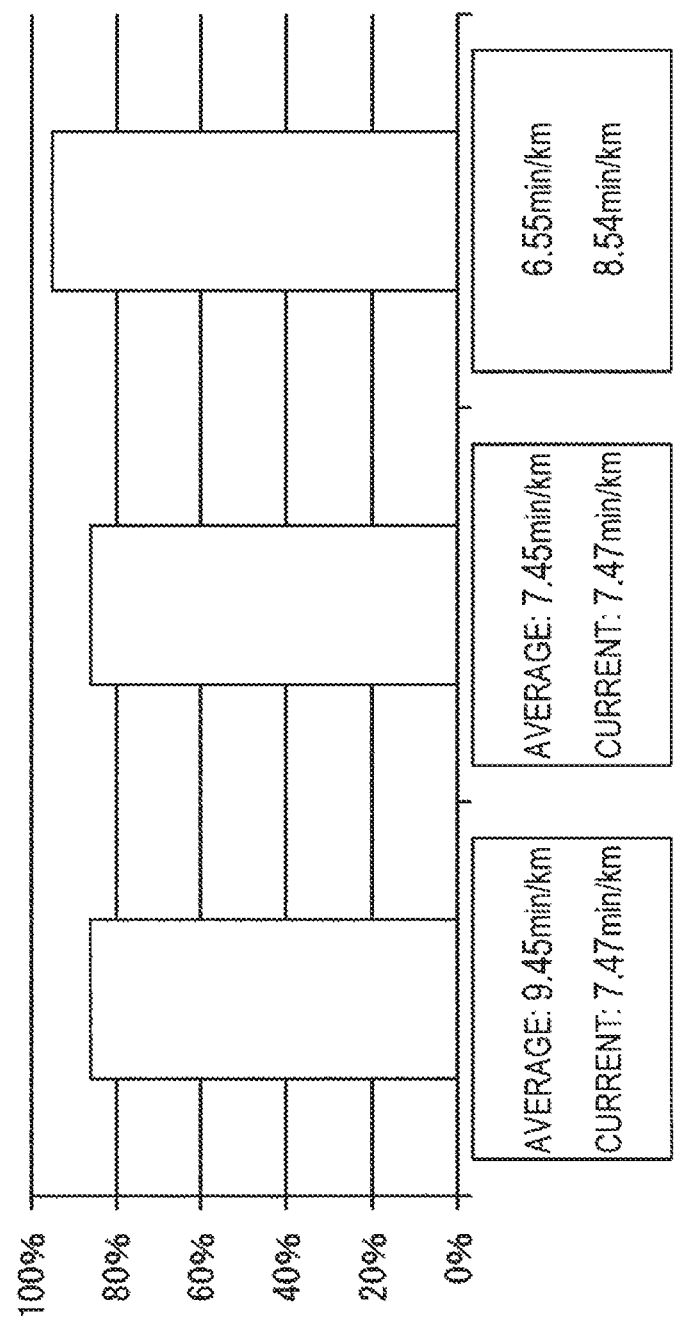

[Fig. 15]
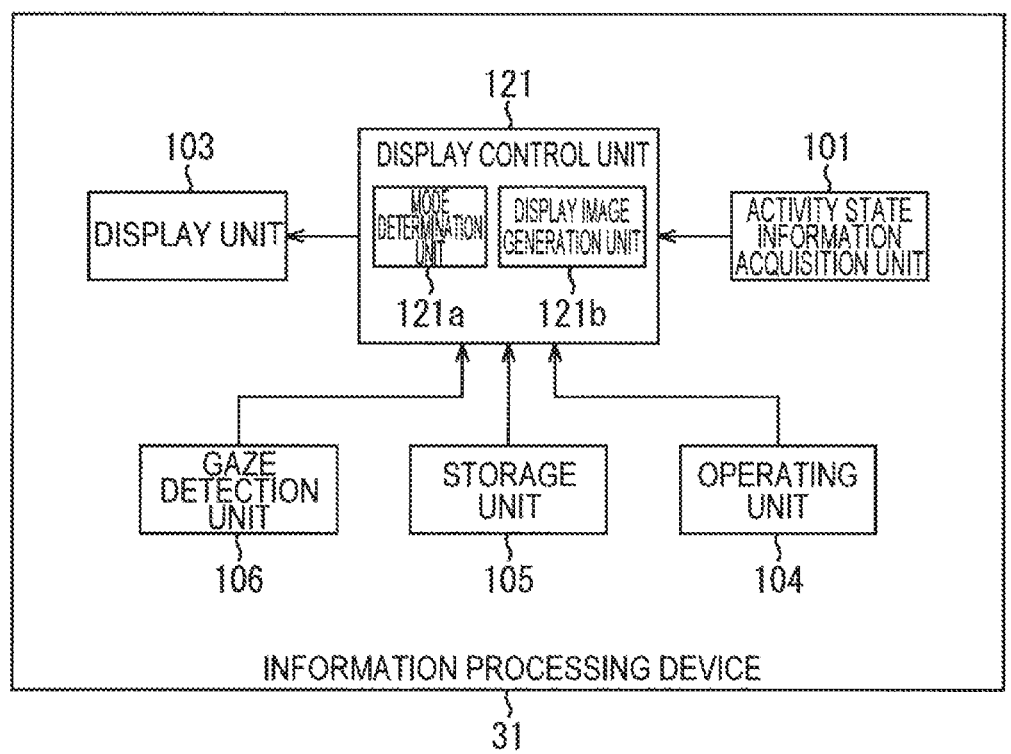

[Fig. 16]
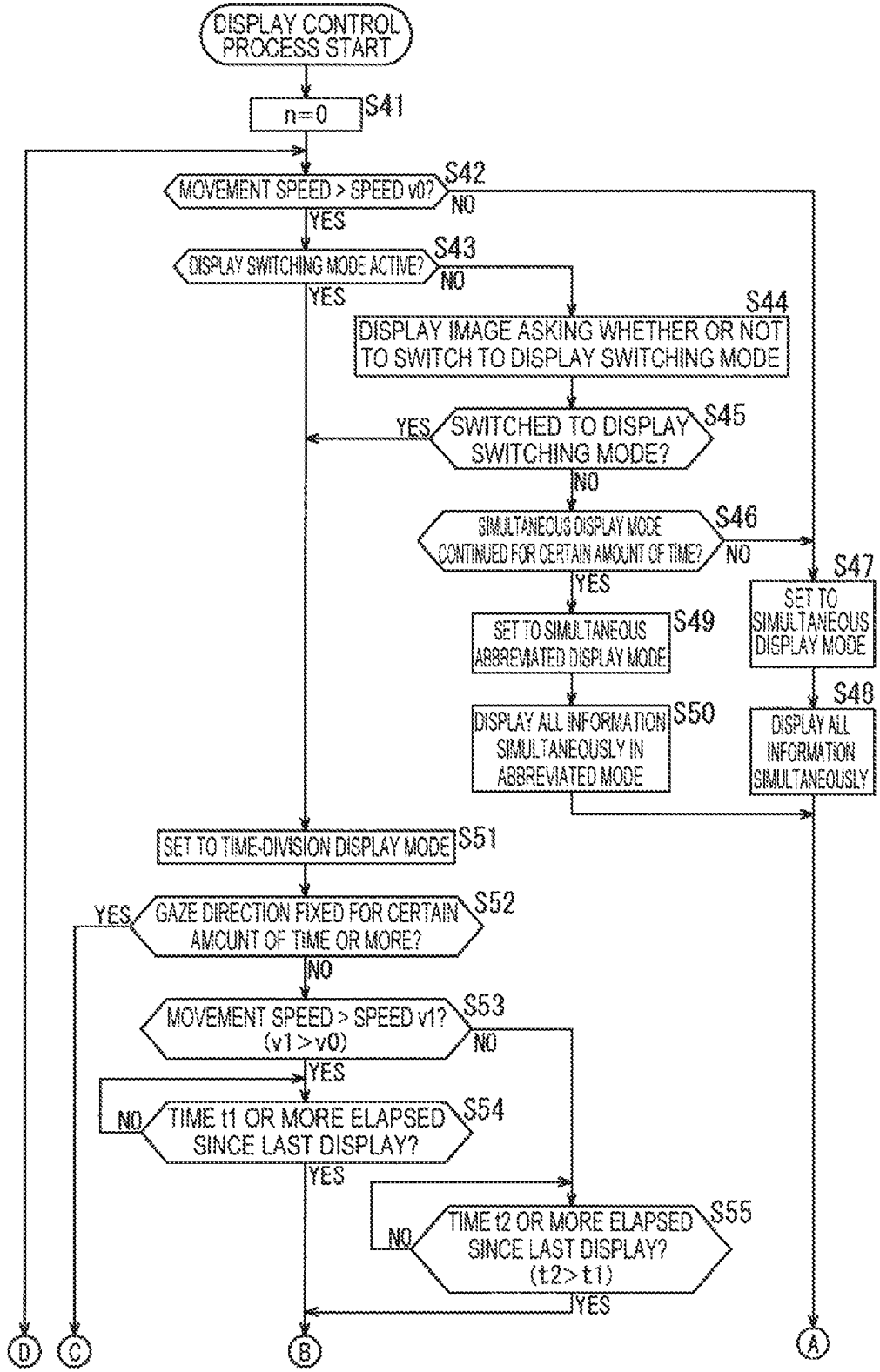

[Fig. 17]
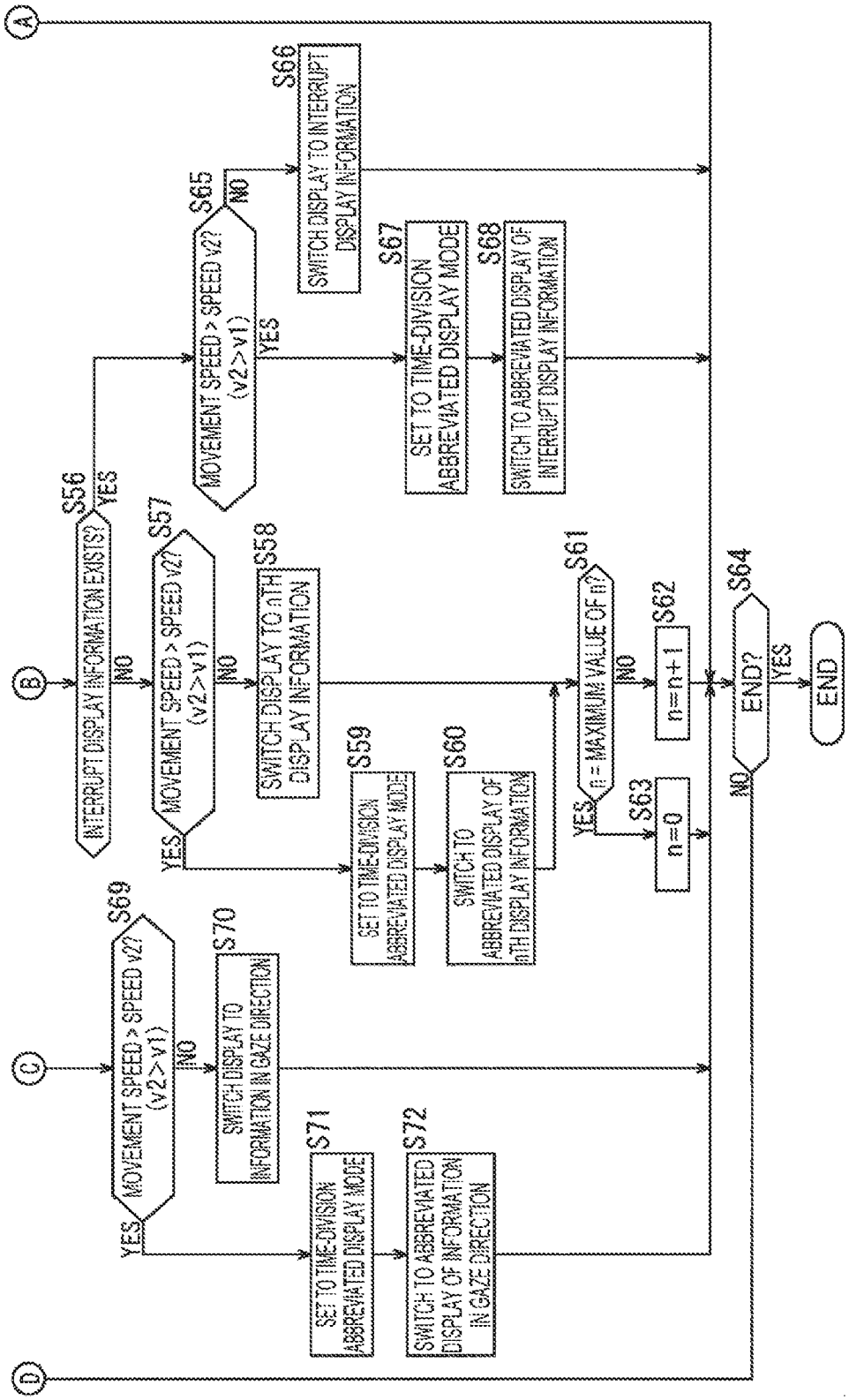

[Fig. 18]
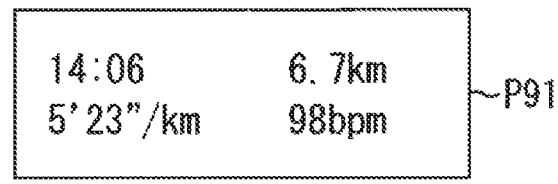
~P91
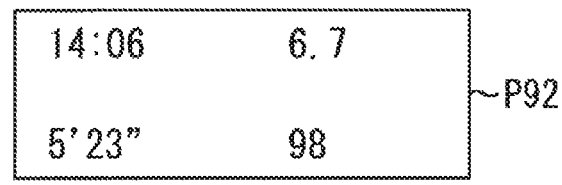
~P92

[Fig. 19]
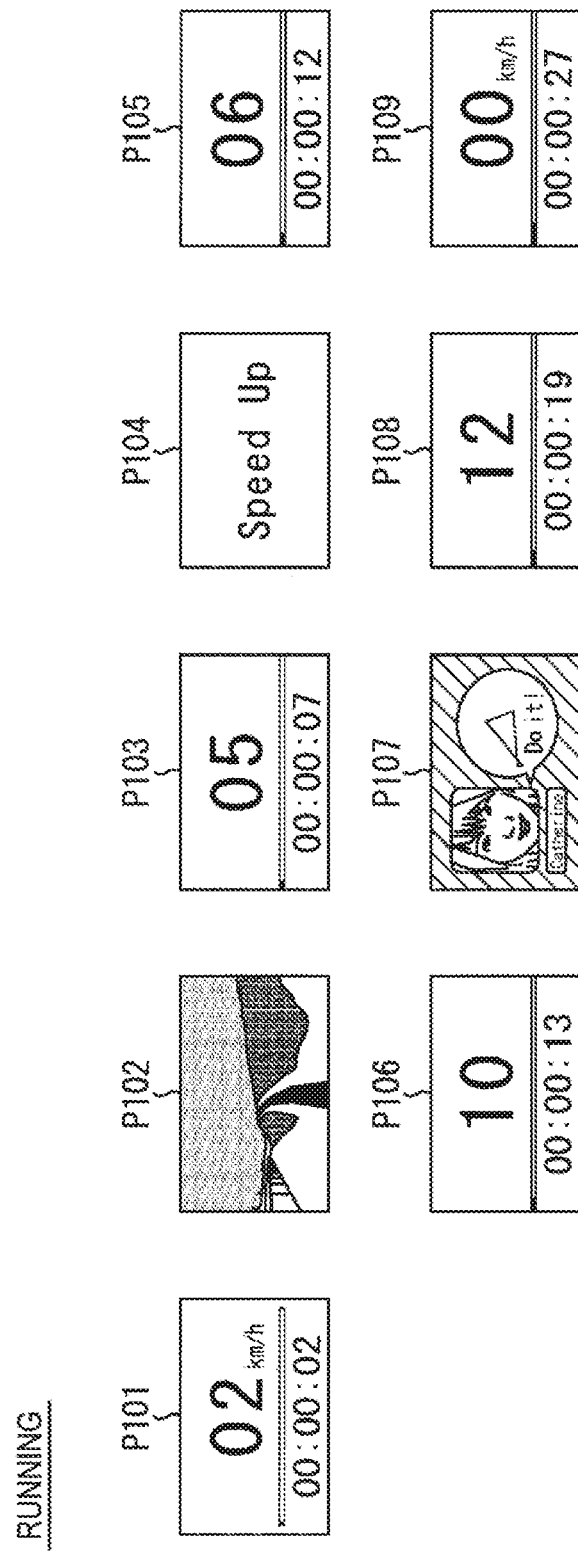

[Fig. 20]

[Fig. 21]
TENNIS
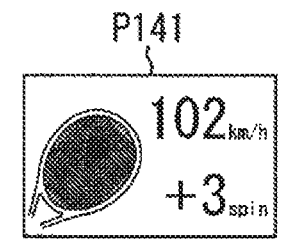
P141
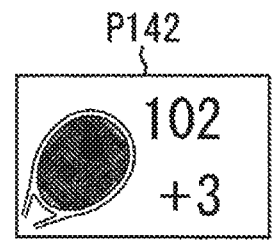
P142

[Fig. 22]
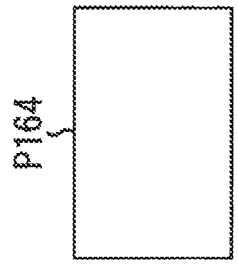
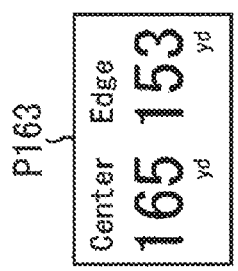
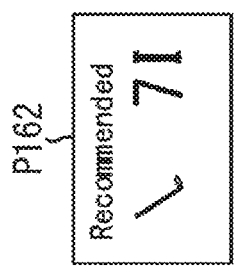
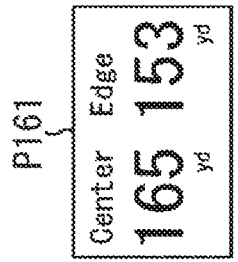

[Fig. 23]
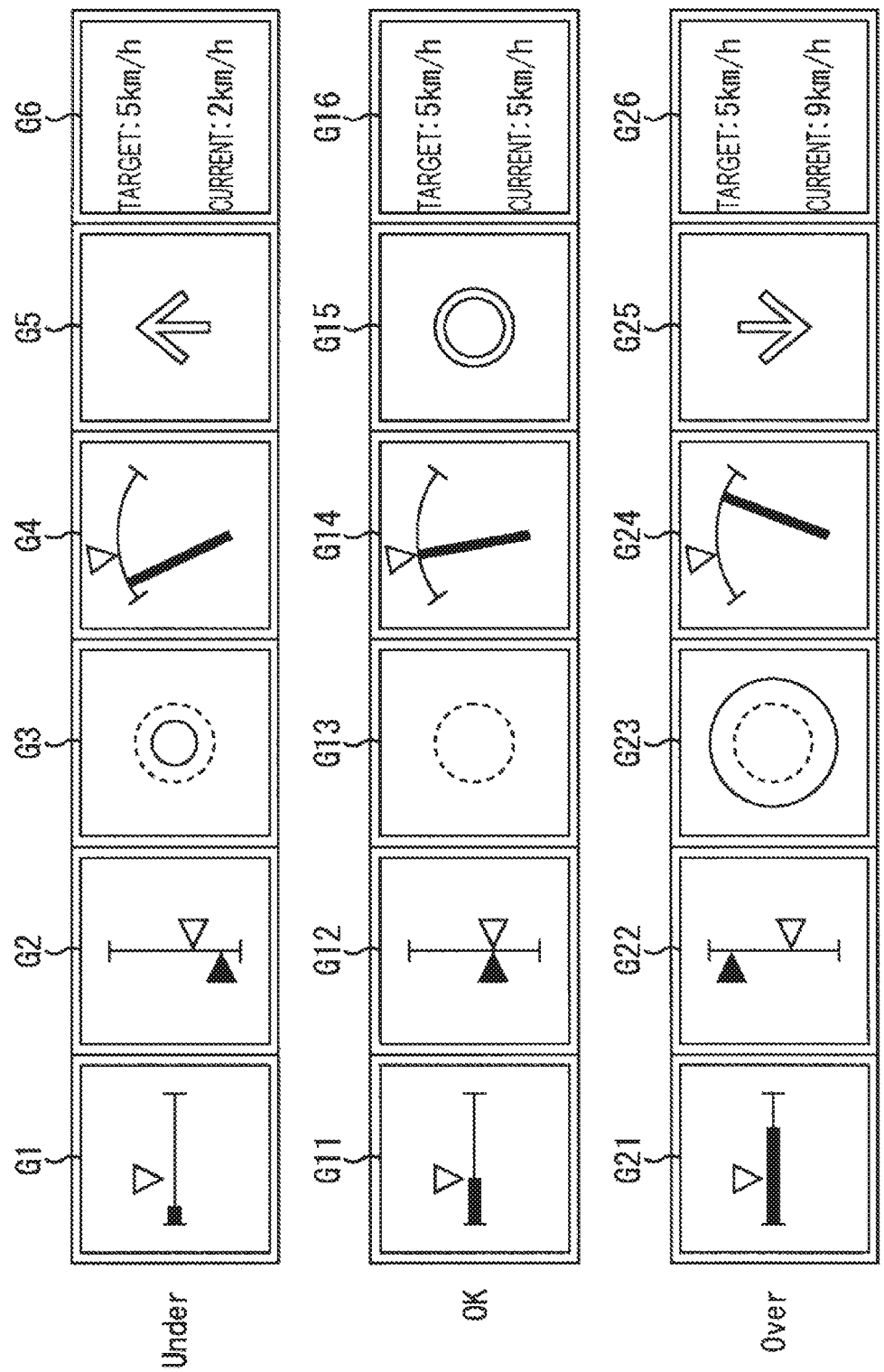

[Fig. 24]
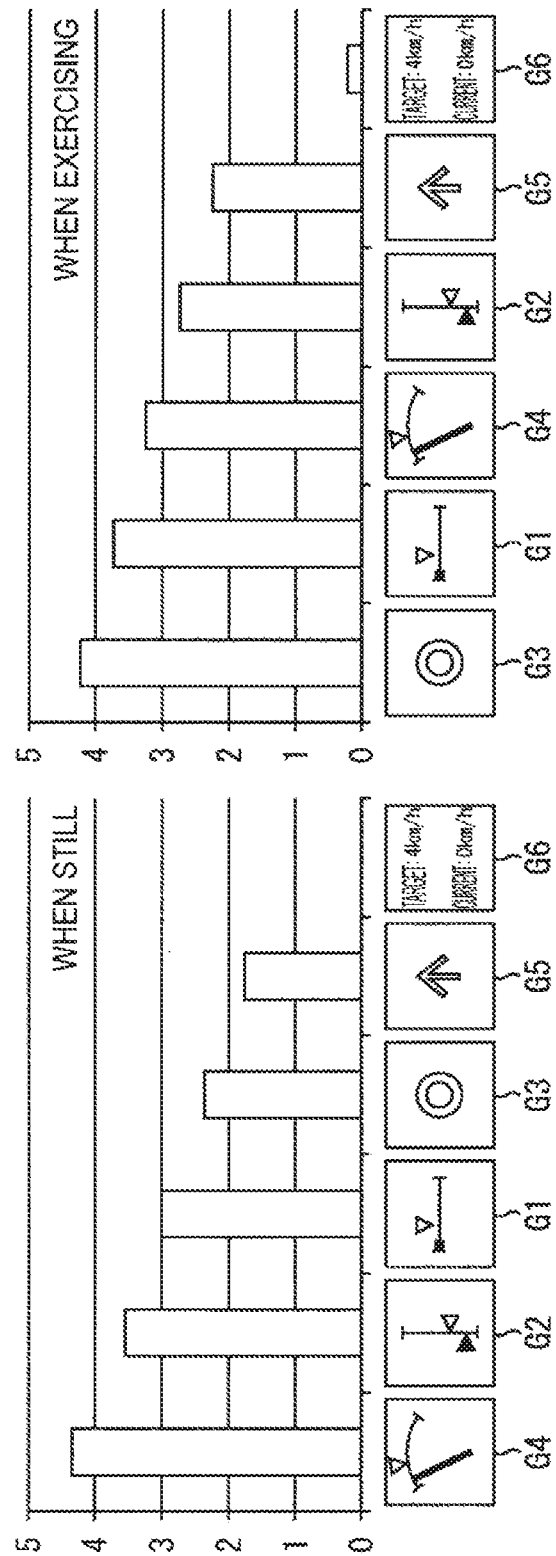

[Fig. 25]
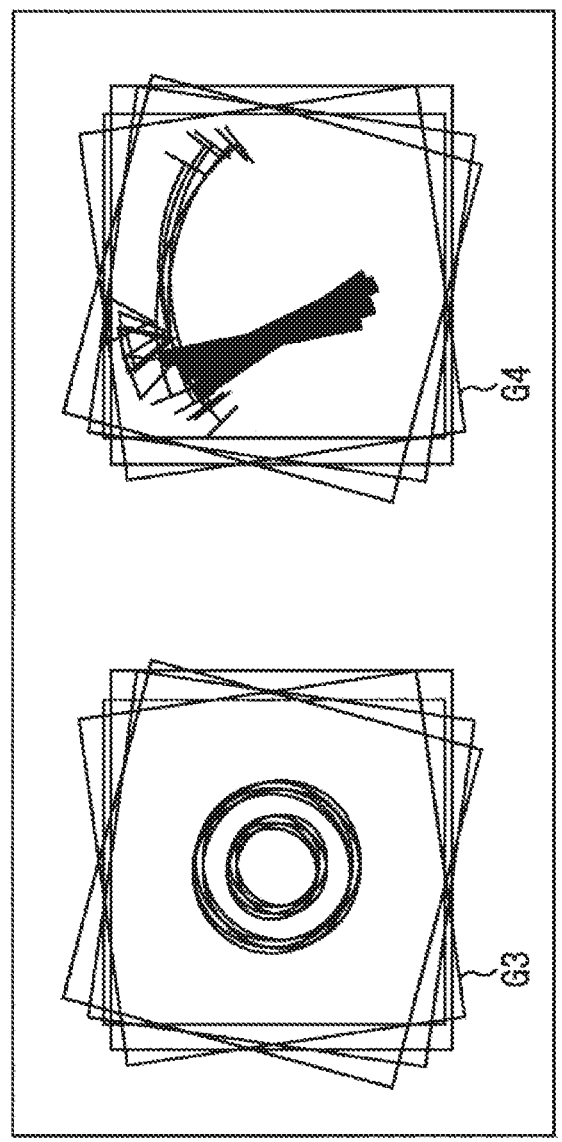

[Fig. 26]
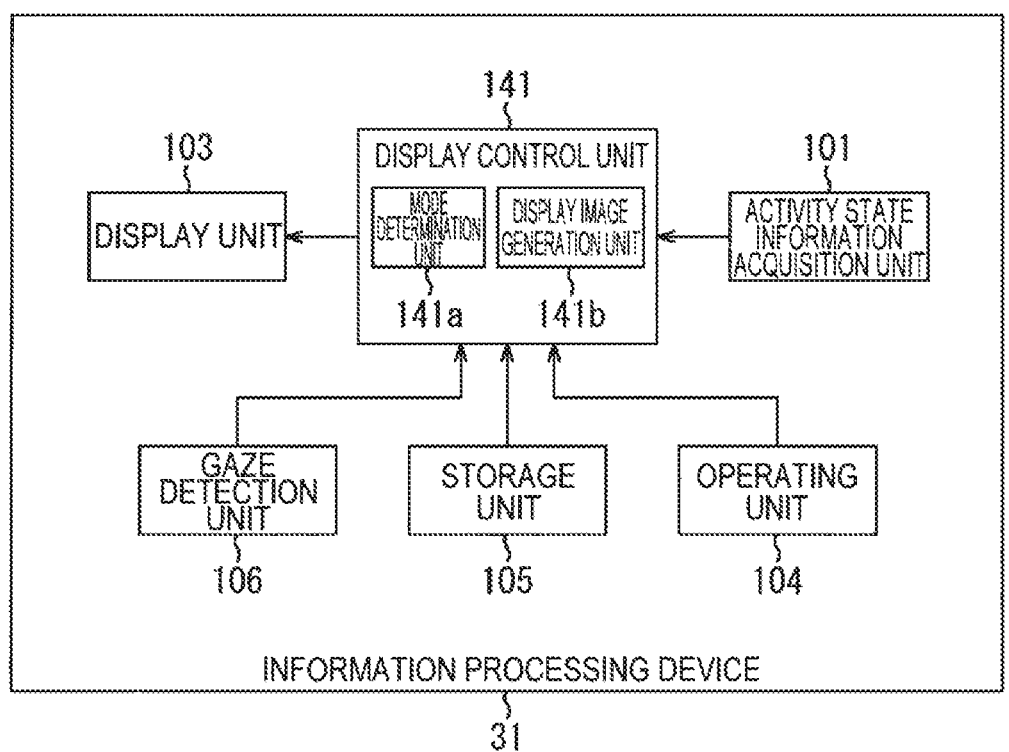

[Fig. 27]
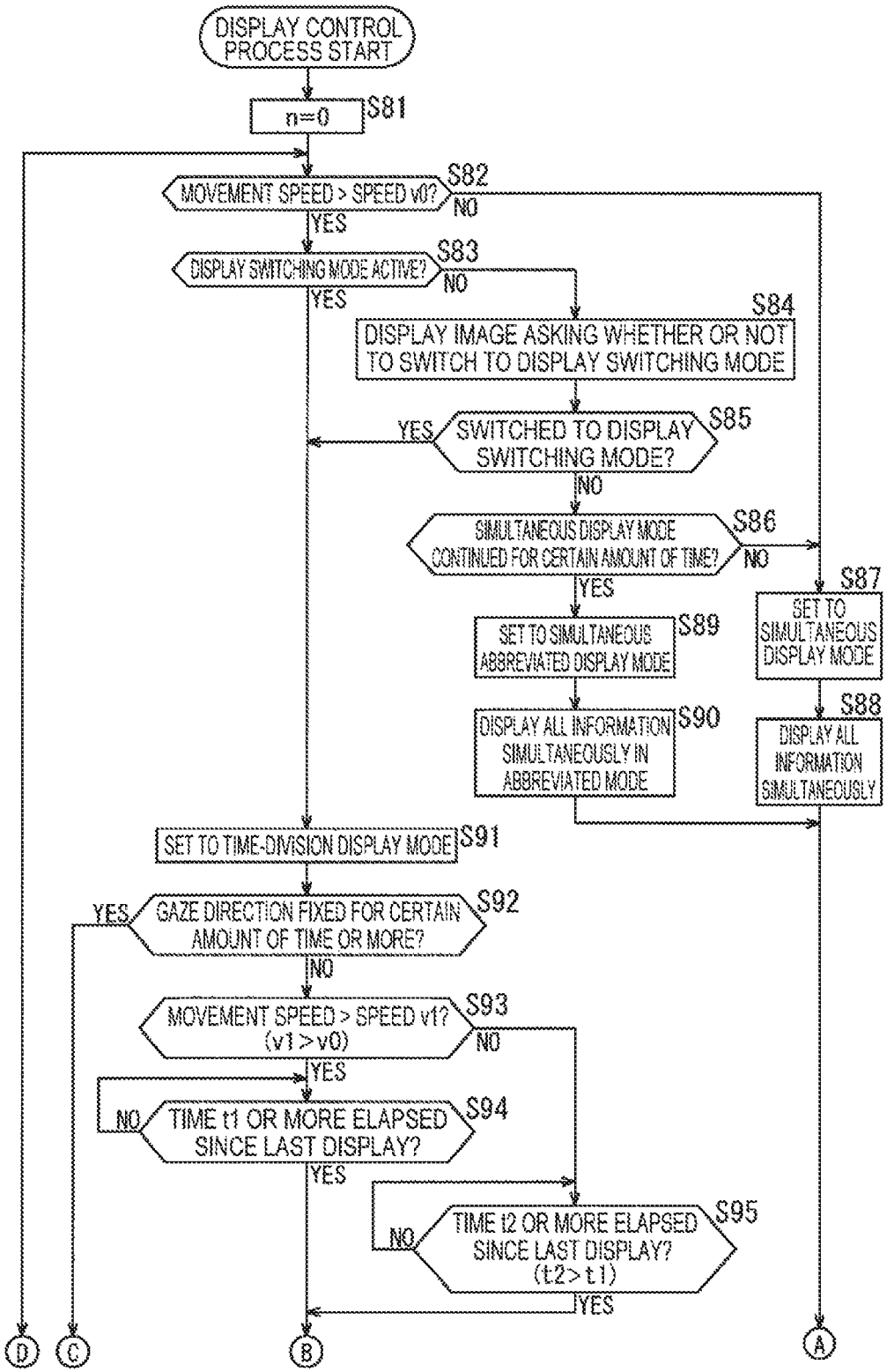

[Fig. 28]
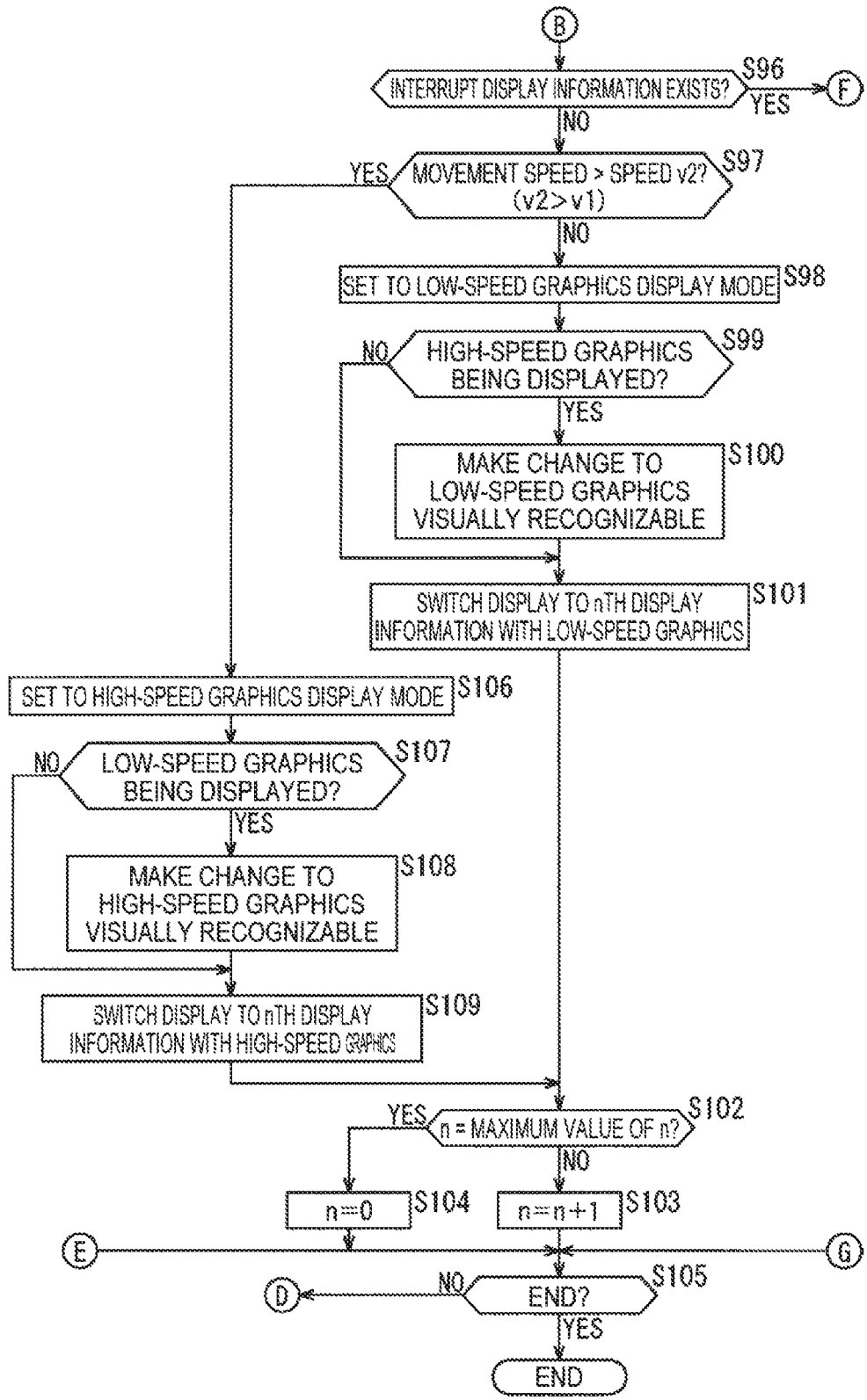

[Fig. 29]
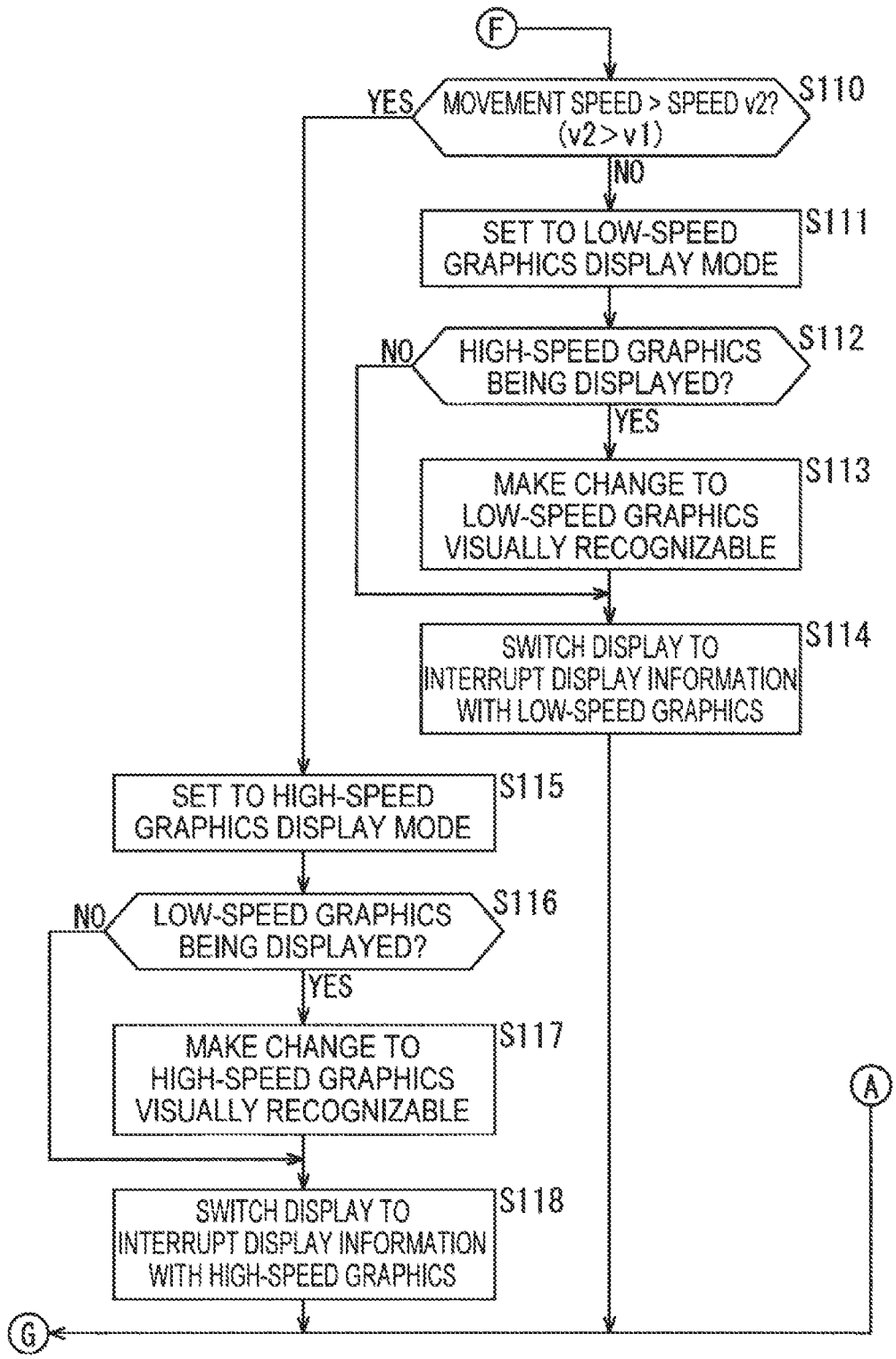

[Fig. 30]
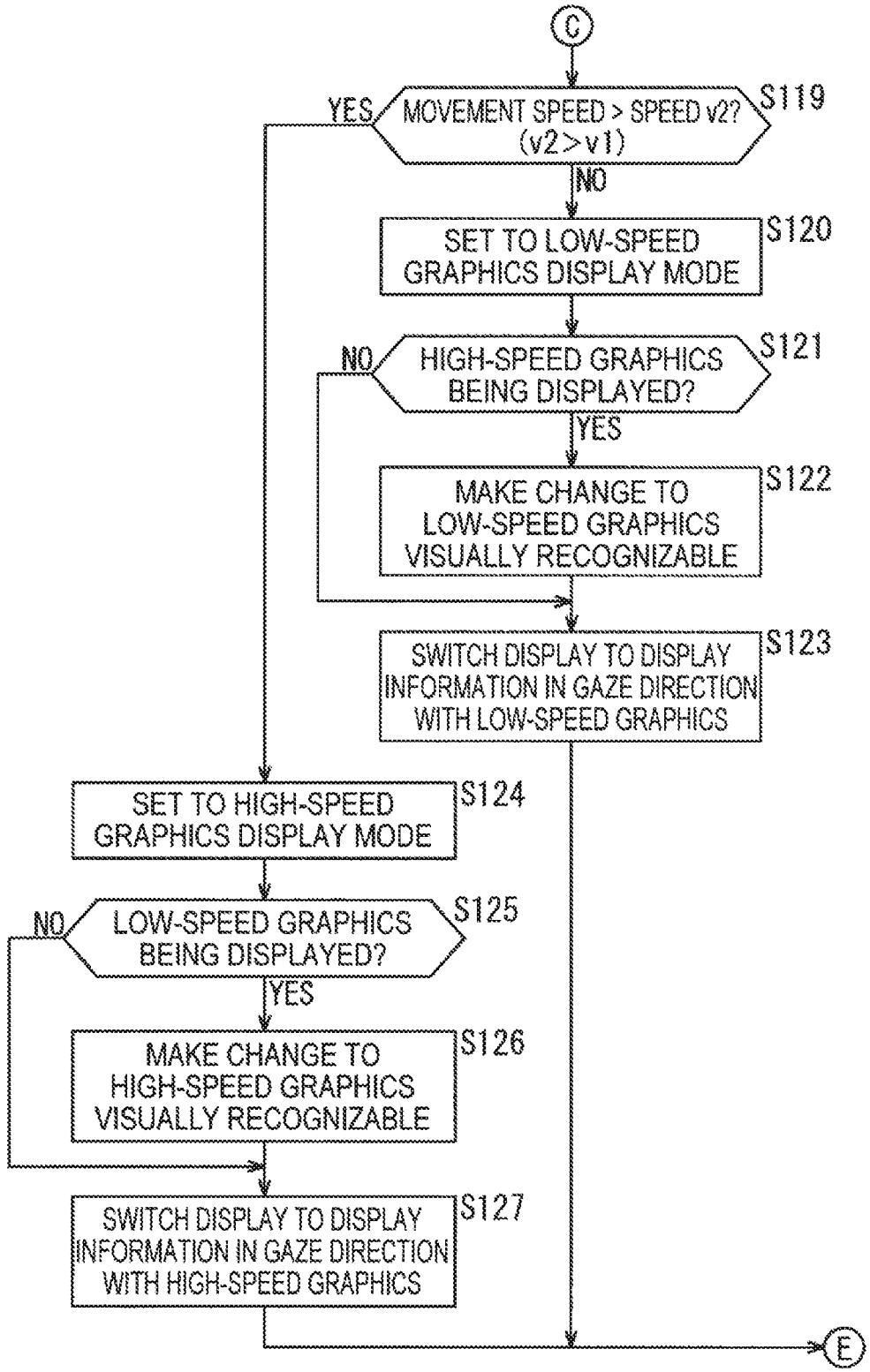

[Fig. 31]
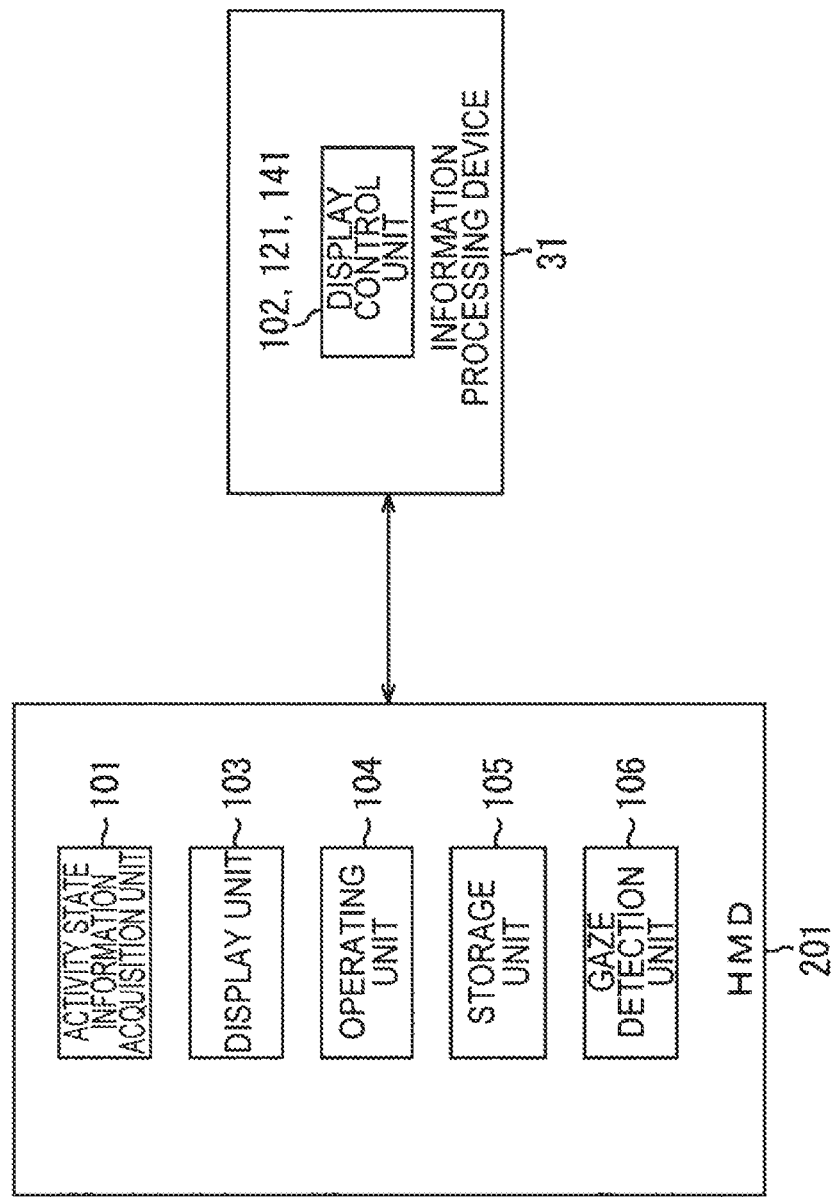

[Fig. 32]
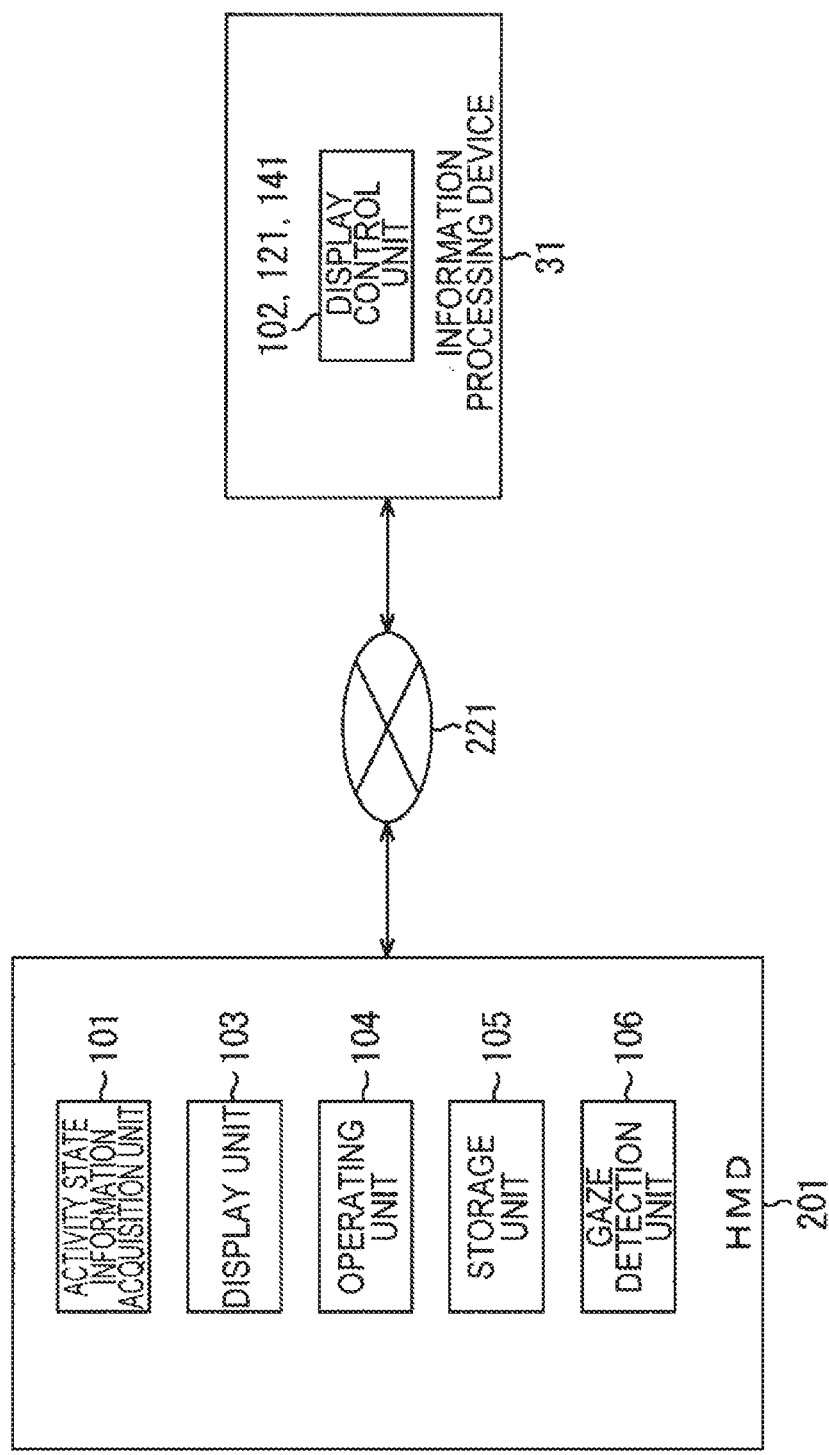

[Fig. 33]
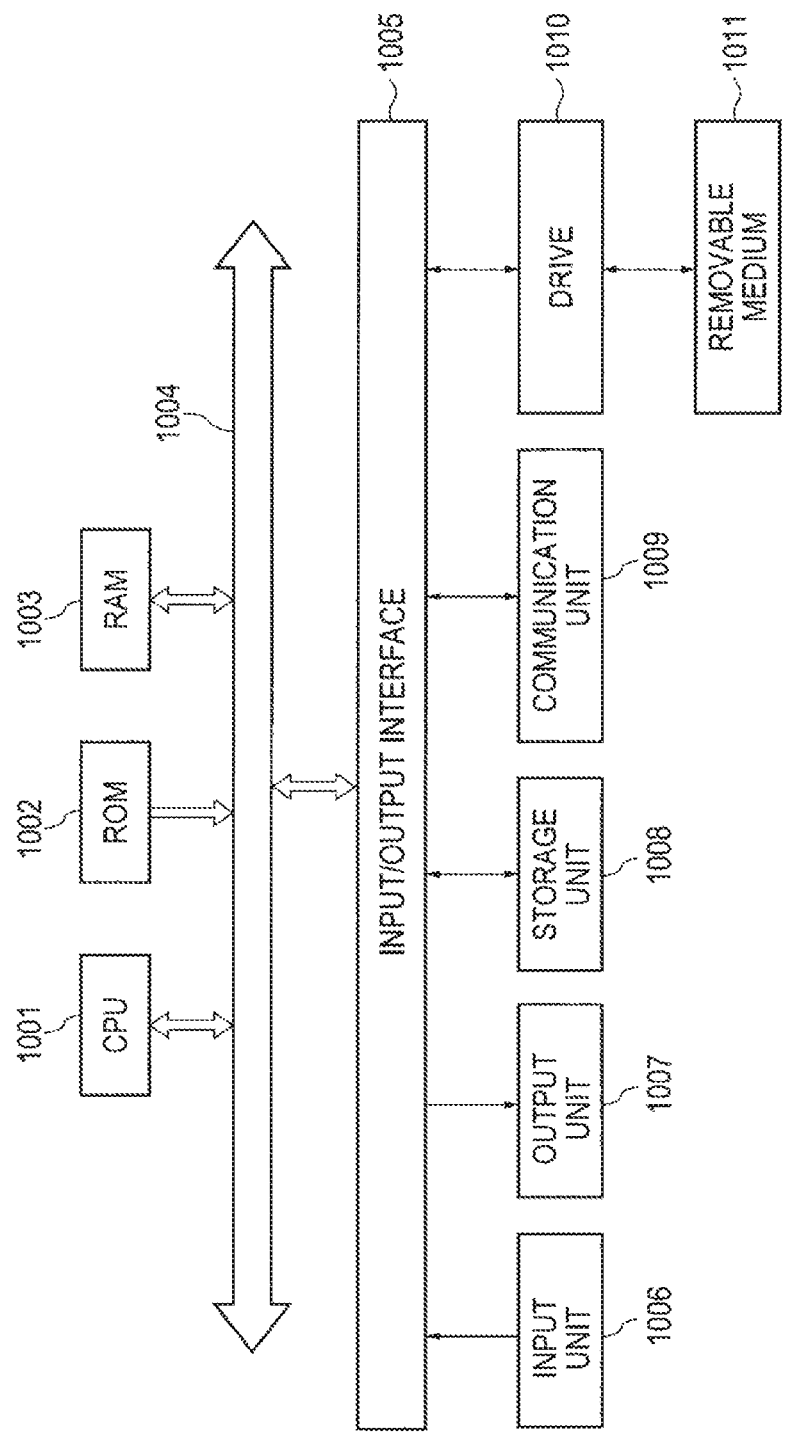

INFORMATION PROCESSING DEVICE, INFORMATION PROCESSING METHOD, AND PROGRAM FOR DECREASING REDUCTION OF VISIBILITY

CROSS REFERENCE TO PRIOR APPLICATION

This application is a National Stage Patent Application of PCT International Patent Application No. PCT/JP2016/077393 (filed on Sep. 16, 2016) under 35 U.S.C. § 371, which claims priority to Japanese Patent Application No. 2015-193420 (filed on Sep. 30, 2015), which are all hereby incorporated by reference in their entirety.

TECHNICAL FIELD

The present disclosure relates to an information processing device, an information processing method, and a program, and more particularly, to an information processing device, an information processing method, and a program configured to minimize the reduction in a user's visibility when exercising while wearing an eyeglasses-style wearable device that displays various information.

BACKGROUND ART

Recently, technical development related to information processing devices worn on the head is being conducted. Such information processing devices include a function of displaying various images to a user wearing the wearable device, as typified by a head-mounted display (HMD), for example.

More specifically, a device that acquires action information, sets a display item corresponding to the action information, and switches to high-priority information for display, for example, has been proposed as the above information processing device (see Patent Document 1).

In addition, a device that plays back and displays a captured video has also been proposed as the above information processing device. In this case, there is also proposed a device that edits the playback speed during playback of the video on the basis of information about the position where the video was captured, and plays back the captured video at the edited playback speed (Patent Document 2).

CITATION LIST

Patent Document

Patent Document 1: JP 2014-071811A
Patent Document 2: JP 2015-128206A

SUMMARY OF THE INVENTION

Problems to be Solved by the Invention

However, in the case of an information processing device worn by the user, such as a wearable device, the user views a displayed imaged while performing various actions with the device being worn, but if the amount of information being displayed is large, visibility is reduced with the technologies proposed in Patent Documents 1 and 2 above, and there is a risk of the user being unable to recognize information appropriately.

The present technology was devised in light of such circumstances, and in particular, is able to minimize the reduction of visibility in an information processing device worn by a user, even when a large amount of information is displayed in various activity conditions.

Solutions to Problems

An information processing device of an embodiment of the present technology is an information processing device including: an activity state information acquisition unit configured to acquire activity state information; and a display mode setting unit configured to set a display mode from among a plurality of display modes on the basis of the activity state information acquired by the activity state information acquisition unit, in which the plurality of display modes includes a first display mode of simultaneously displaying first information and second information different from the first information, and a second display mode of displaying the first information and the second information at different timing.

The plurality of display modes can include the first display mode of simultaneously displaying the first information and the second information, and the second display mode of displaying the first information and the second information at different timing in separate time periods.

The plurality of display modes can include the first display mode of simultaneously displaying the first information and the second information, and the second display mode of displaying the first information at first timing and displaying the second information at second timing different from the first timing, the first timing and the second timing not being overlapped with each other.

The activity state information can include user's exercise intensity.

The user's exercise intensity can be specified by measurement of movement speed, vibration, gaze, heart rate, body temperature, perspiration, brain waves, or myoelectric potential of the user.

The display mode setting unit can set the first display mode of simultaneously displaying the first information and the second information in a case where the exercise intensity is weaker than a first certain threshold value, and can set the second display mode of displaying the first information and the second information at different timing in separate time periods in a case where the exercise intensity is stronger than the first certain threshold value.

The display mode setting unit can set display time, during which the first information and the second information are displayed, according to the exercise intensity in a case where the exercise intensity is stronger than the first certain threshold value and the second display mode of displaying the first information and the second information at different timing in separate time periods is set.

In a case where the exercise intensity is stronger than the first certain threshold value and the second display mode of displaying the first information and the second information at different timing in separate time periods is set, the display mode setting unit can set that the certain number of pieces of information are displayed each for first display time if the exercise intensity is weaker than a second certain threshold value larger than the first certain threshold value, and can set that the first information and the second information are displayed for second display time if the exercise intensity is stronger than the second certain threshold value.

The first display time can be shorter than the second display time.

The first display time can be longer than the second display time.

In a case where the exercise intensity is stronger than the first certain threshold value and the second display mode of displaying the first information and the second information at different timing in separate time periods is set, the display mode setting unit can set that the certain number of pieces of information are displayed each for first display time if the exercise intensity is weaker than a second certain threshold value larger than the first certain threshold value, and can set that the first information and the second information are displayed for second display time if the exercise intensity is stronger than the second certain threshold value larger than the first certain threshold value.

The display mode setting unit can set display time, during which the first information and the second information are displayed, according to importance of information to be displayed.

The plurality of display modes can include the first display mode of simultaneously displaying the first information and the second information, and the second display mode of displaying the first information and the second information at different timing according to the exercise intensity on the basis of user's operation contents.

A display image generation unit configured to generate an image according to the display mode set by the display mode setting unit can be further provided.

A display unit configured to display an image that can be seen along with an outside world can be further provided, and the display unit can display, as the display image, the image generated by the display image generation unit according to the display mode set by the display mode setting unit.

The display unit can further include displaying of the display image displayed by an eyepiece optical system in which a length in a direction, which is shorter than the other directions, of a region where light is emitted towards user's pupil is shorter than or equal to an upper limit of pupil diameter variation.

The display mode setting unit can control displaying of a mobile terminal.

An information processing method of an embodiment of the present technology includes the steps of: acquiring activity state information; and setting a display mode from among a plurality of display modes on the basis of the acquired activity state information, in which the plurality of display modes includes a first display mode of simultaneously displaying first information and second information different from the first information, and a second display mode of displaying the first information and the second information at different timing.

A program of an embodiment of the present technology is a program including: an activity state information acquisition unit to acquire activity state information; and a display mode setting unit to set a display mode from among a plurality of display modes on the basis of the activity state information acquired by the activity state information acquisition unit, in which the plurality of display modes includes a first display mode of simultaneously displaying first information and second information different from the first information, and a second display mode of displaying the first information and the second information at different timing.

In an embodiment of the present technology, activity state information is acquired and a display mode is set from among a plurality of display modes on the basis of the acquired activity state information. The plurality of display modes includes a first display mode of simultaneously displaying first information and second information different from the first information, and a second display mode of displaying the first information and the second information at different timing.

An information processing device of an embodiment of the present technology may be an independent device or a block that functions as an information processing device.

Effects of the Invention

According to an embodiment of the present technology, in an information processing device worn by a user, it is possible to minimize a reduction of visibility even in various activity conditions.

BRIEF DESCRIPTION OF DRAWINGS

FIG. 1 is a diagram explaining the exterior appearance of an information processing device applying an embodiment of the present technology.

FIG. 2 is a perspective view illustrating an example configuration of a light guide unit of the information processing device of FIG. 1.

FIG. 3 is a cross-section view illustrating an example configuration of a light guide unit of the information processing device of FIG. 1.

FIG. 4 is a diagram illustrating an example of a state in which the information processing device of FIG. 1 is worn by a user.

FIG. 5 is a block diagram explaining a first embodiment of functions realized by the information processing device of FIG. 1.

FIG. 6 is a diagram explaining a procedure when a user wearing the information processing device of FIG. 1 views something.

FIG. 7 is a diagram explaining the relationship between the layout when information is displayed by the information processing device of FIG. 1, and the recognition rate depending on the activity state.

FIG. 8 is a diagram explaining a simultaneous display mode and a time-division display mode.

FIG. 9 is a flowchart explaining a display control process by the information processing device of FIG. 5.

FIG. 10 is a display example by an application used when running, presented on a display image displayed by a display control process by the information processing device of FIG. 5.

FIG. 11 is a display example by an application used when cycling, presented on a display image displayed by a display control process by the information processing device of FIG. 5.

FIG. 12 is a display example by an application used when playing tennis, presented on a display image displayed by a display control process by the information processing device of FIG. 5.

FIG. 13 is a display example by an application used when playing golf, presented on a display image displayed by a display control process by the information processing device of FIG. 5.

FIG. 14 is a diagram explaining the relationship between the layout when information is displayed by the information processing device of FIG. 1, and the recognition rate depending on whether or not labels and units are omitted.

FIG. 15 is a block diagram explaining a second embodiment of functions realized by the information processing device of FIG. 1.

FIG. 16 is a flowchart explaining a display control process by the information processing device of FIG. 15.

FIG. 17 is a flowchart explaining a display control process by the information processing device of FIG. 15.

FIG. 18 is a display example on a display image displayed by a display control process by the information processing device of FIG. 15.

FIG. 19 is a display example by an application used when running, presented on a display image displayed by a display control process by the information processing device of FIG. 15.

FIG. 20 is a display example by an application used when cycling, presented on a display image displayed by a display control process by the information processing device of FIG. 15.

FIG. 21 is a display example by an application used when playing tennis, presented on a display image displayed by a display control process by the information processing device of FIG. 15.

FIG. 22 is a display example by an application used when playing golf, presented on a display image displayed by a display control process by the information processing device of FIG. 15.

FIG. 23 is a diagram explaining an example of graphics displayed by the information processing device of FIG. 1.

FIG. 24 is a diagram explaining the difference in recognition rates between standing still and moving for the example graphics of FIG. 23.

FIG. 25 is a diagram explaining the difference in recognition rates between standing still and moving for the example graphics of FIG. 23.

FIG. 26 is a block diagram explaining a third embodiment of functions realized by the information processing device of FIG. 1.

FIG. 27 is a flowchart explaining a display control process by the information processing device of FIG. 26.

FIG. 28 is a flowchart explaining a display control process by the information processing device of FIG. 26.

FIG. 29 is a flowchart explaining a display control process by the information processing device of FIG. 26.

FIG. 30 is a flowchart explaining a display control process by the information processing device of FIG. 26.

FIG. 31 is a block diagram illustrating another functional configuration example of the first embodiment to the third embodiment.

FIG. 32 is a block diagram illustrating yet another functional configuration example of the first embodiment to the third embodiment.

FIG. 33 is a diagram explaining an example configuration of a general-purpose personal computer.

MODE FOR CARRYING OUT THE INVENTION

First Embodiment

First, an overview of an information processing device according to the first embodiment of the present technology will be described with reference to FIG. 1.

FIG. 1 is an exterior view of an information processing device according to the first embodiment of the present technology.

The information processing device 31 is equipped with an image display function, and is worn on the head of the human body. Specifically, the information processing device 31 is a wearable device having an image display function of emitting image light directly onto the user's eyes through a lens, and the formed virtual image is recognized by the user as an image. In other words, the information processing device 31 functions as a head-mounted display (HMD).

Furthermore, an eyepiece optical system that shines image light is positioned in front of the user's eye when the information processing device 31 is worn by the user, and is smaller than the average human pupil diameter. For this reason, not only image light but also outside light shines on the pupil of the user wearing the information processing device 31, and thus both an image and the outside world enter the user's field of vision.

For example, as illustrated in FIG. 1, the information processing device 31 includes a main unit 41, an arm 42, and a light guide reflection unit 43 having an eyepiece window that emits image light. Additionally, the light guide reflection unit 43 is provided as an eyepiece optical system so that the length in a direction whose length is shorter than the other directions in the region of the light guide reflection unit 43 where light is emitted towards the user's pupil (hereinafter also called the width in the short direction) is narrower than the pupil diameter. Note that the information processing device 31 may be attached to eyeglasses 11 or the like.

The main unit 41 is connected to the arm 42 and the eyeglasses 11. Specifically, the lengthwise edge of the main unit 41 is joined to the arm 42, and one side face of the main unit 41 is attached to the eyeglasses 11 via a connecting member. Note that the main unit 41 may also be worn directly on the head of the human body.

In addition, the main unit 41 includes a built-in control board for controlling the operation of the information processing device 31. Specifically, the main unit 41 includes a control board including components such as a central processing unit (CPU) and random access memory (RAM), and is connected to the light guide reflection unit 43 through the arm 42 using signal wires or the like.

The arm 42 connects the main unit 41 and the light guide reflection unit 43, and supports the light guide reflection unit 43. Specifically, the arm 42 is respectively joined to one end of the main unit 41 and one end of the light guide reflection unit 43, and secures the light guide reflection unit 43. Also, the arm 42 includes built-in signal wires for communicating image-related data provided from the main unit 41 to the light guide reflection unit 43.

The light guide reflection unit 43 projects image light outside the information processing device 31. Specifically, the light guide reflection unit 43 projects image light provided from the main unit 41 via the arm 42 outside the information processing device 31 through an eyepiece lens 61 (FIG. 2), or in other words, towards an eye of the user wearing the information processing device 31.

In addition, an operating unit 41a made up of a touch sensor is provided on the top face as seen in the drawing. The operating unit 41a accepts operating input, such as a swipe in the direction of the solid arrow in the drawing, or a tap in the direction of the dashed arrow, and produces a corresponding operation signal.

Note that the configuration of the operating unit 41a may include not only the configuration enabling touch operations such as swiping and tapping as discussed above, but also another configuration able to accept operating input. For example, the operating unit 41a may also be configured to accept an input operation performed by contacting a physically configured operating button or the like, or be configured to accept non-contacting operating input. For example, the operating unit 41a may be a combination of all or some of an infrared (IR) communication or capacitive sensor (proximity sensor), a camera (image sensor), and a photodiode.

In addition, on the end on the main unit 41 connected to the arm 42, an outward-facing camera 42b able to capture images of the user's nearby environment is provided, and images captured by this outward-facing camera 42b may be emitted and projected onto the pupil by the light guide reflection unit 43, or captured images may be used to detect objects in the user's nearby environment, as well as to detect the position and orientation of such objects.

Next, FIGS. 2 to 4 will be referenced to describe an example configuration of the light guide reflection unit 43 in detail. FIG. 2 is a perspective view illustrating an example of a diagrammatic configuration of the light guide reflection unit 43 in the information processing device 31 according to the present embodiment, while FIG. 3 is a cross-section view illustrating an example of a diagrammatic configuration of the light guide reflection unit 43 in the information processing device 31 according to the present embodiment. Also, FIG. 4 is a diagram illustrating an example of a state in which the light guide reflection unit 43 of the information processing device 31 according to the present embodiment is worn by the user.

As illustrated in FIGS. 2 and 3, the light guide reflection unit 43 includes, as an eyepiece optical system, a projection unit 71, a light guide unit 51, a reflection unit 72, an eyepiece lens 61, and an imaging unit 73.

The projection unit 71 emits image light towards the light guide unit 51. For example, the projection unit 71 is a display panel that displays an image provided from the main unit 41 as illustrated in FIG. 3, and by the display of an image, emits light towards the light guide unit 51.

The light guide unit 51 guides incident image light to the reflection unit 72. For example, the light guide unit 51 is a columnar member as illustrated in FIG. 2, and guides image light so that the image light projected from the projection unit 71 reaches the reflection unit 72, as illustrated in FIG. 3. Note that the light guide unit 51 may be a tubular member which a hollow interior, or a transparent member that transmits image light.

The reflection unit 72 reflects arriving image light towards the eyepiece lens 61. For example, as illustrated in FIG. 3, the reflection unit 72 reflects image light guided by the light guide unit 51 to head towards the position of the eyepiece lens 61.

The eyepiece lens 61 enlarges the image. Specifically, the eyepiece lens 61 refracts the image light reflected by the reflection unit 72 to enlarge the image according to the image light.

In addition, the light guide reflection unit 43 is formed so that the length in a direction whose length is shorter than the other directions in the region where light is emitted towards the user's pupil is a length less than or equal to the upper limit of pupil diameter variation. Specifically, the light guide reflection unit 43 is formed so that the width in the short direction of the light guide reflection unit 43 is less than or equal to an average pupil diameter. For example, as illustrated in FIG. 4, the light guide reflection unit 43 is formed so that the width L2 in the short direction of the light guide reflection unit 43 is less than or equal to the average pupil diameter L1. Note that since the pupil diameter L1 of a person generally varies over a range from approximately 2 mm to 8 mm, L2 is configured to be 8 mm or less, such as approximately 4 mm, for example. Also, the shape of the light guide reflection unit 43, namely the region from which light is emitted, may be not only rectangular, but also circular, elliptical, or some other polygonal shape.

To recognize the user's gaze direction, the imaging unit 73 captures the user's eye, particularly the position of the eye, and supplies the captured image to the information processing device 31.

Note that in FIG. 1, the information processing device 31 uses a method (hereinafter also called the eye-division method) enabling the user to view an image (hereinafter also called the display image) displayed by projection with the light guide reflection unit 43 onto a partial region of the user's eye, while also enabling the user to view the outside world in all other regions.

However, the information processing device 31 may also use a method other than the eye-division method insofar as the configuration enables the user to view the outside world and the display image simultaneously. For example, the information processing device 31 may also use a method that displays a display image on a partial region of the lens part of the eyeglasses, and enables viewing of the outside world by allowing light from the outside world to be transmitted from all other regions (transmissive method), or a method that presents a display image in part of an image of the outside world for display on a display provided so as to cover the entire surface of the eye (video see-through method).

<Example Configuration of Functions Realized by Information Processing Device of FIG. 1>

Next, FIG. 5 will be referenced to describe an example configuration of the functions of the information processing device 31 according to the present embodiment. FIG. 5 is a block diagram for explaining the functions realized by the information processing device 31 according to the present embodiment.

As illustrated in FIG. 5, the information processing device 31 is equipped with an activity state information acquisition unit 101, a display control unit 102, a display unit 103, an operating unit 104, a storage unit 105, and a gaze detection unit 106.

The activity state information acquisition unit 101 acquires activity state information indicating the activity state of the user. Specifically, the activity state information includes an exercise intensity indicating the strenuousness of a person's activity state, according to which the user's gaze varies.

Herein, exercise intensity is, for example, the user's movement speed (including acceleration and speed in a certain direction, or alternatively, a speed computed using an acceleration obtained from a time series of position information), vibration (include amplitude and period), as well as biosensing results such as gaze, heart rate, body temperature, amount of perspiration, brain waves, or myoelectric potential.

More specifically, a strong exercise intensity means that the strenuousness of a person's activity state is strong (high), indicating a state in which the user's movement speed is fast, the number of vibrations is high, the heart rate is high, the body temperature is high, or the amount of perspiration is large, for example. Conversely, a weak exercise intensity means that the strenuousness of a person's activity state is weak (low), and is a state in which the user's movement speed is slow, the number of vibrations is low, the heart rate is low, the body temperature is low, or the amount of perspiration is small, for example.

In addition, the activity state information acquisition unit 101 may also be configured to be able to recognize the user's actions on the basis of activity state information, namely the exercise intensity. Specifically, the activity state information acquisition unit 101 may be configured to recognize a specific exercise state, such as the user walking, running, or taking an elevator, on the basis of activity state information including exercise intensity.

In addition, the activity state information acquisition unit 101 acquires content set manually by the user according to operation content of the operating unit 104. More specifically, the activity state information acquisition unit 101 is able to recognize a type of application from among tennis, running, and cycling applications as content information according to operation content of the operating unit 104. For example, a communication device (not illustrated) such as Bluetooth (registered trademark) may be provided, and when communication is enabled between this communication device and a sensor provided in a shoe or the like, such as a position information detecting sensor, an acceleration sensor, or a vibration sensor, for example, the activity state information acquisition unit 101 is able to recognize that the type of application corresponds to running.

Note that the following description will proceed under the supposition that the activity state information is an exercise intensity indicating the strenuousness of exercise according to the user's activity state. Namely, suppose that the activity state information acquisition unit 101 acquires the movement speed of the information processing device 31 as the exercise intensity, and supplies the acquired movement speed to the display control unit 102. Also, the acceleration may be acquired as the exercise intensity, and the movement speed may be computed from the acquired acceleration.

The operating unit 104, upon receiving an operation signal supplied by the operating unit 41a, recognizes operation content, and supplies information about the recognized operation content to the display control unit 102.

The storage unit 105 stores image format information about the format of images to be displayed by an application. The display control unit 102 reads out an image format stored in the storage unit 105, performs processing such as adding information depending on the application, and outputs to the display unit 103 for display.

The gaze detection unit 106 recognizes the user's gaze direction on the basis of an eye image supplied by the imaging unit 73, and supplies information about the recognized gaze direction to the display control unit 102.

The display control unit 102 controls the display on the display unit 103 by generating a display image to be displayed on the basis of the activity state information supplied by the activity state information acquisition unit 101, the operation content supplied by the operating unit 104, the gaze direction supplied by the gaze detection unit 106, and an image that acts as the format set per application and stored in the storage unit 105, and outputting to the display unit 103 for display.

More specifically, the display control unit 102 is equipped with a mode determination unit 102a and a display image generation unit 102b. The mode determination unit 102a determines and sets a display mode for the display image, on the basis of the activity state information, namely the exercise intensity. In addition, on the basis of the activity state information, the mode determination unit 102a may recognize the user's activity content, namely an activity such as walking, running, playing tennis, or playing golf, for example, and determine the display mode of the display image according to the recognized activity content. The display image generation unit 102b generates a display image corresponding to the display mode set by the mode determination unit 102a, and displays the display image on the display unit 103. Note that the display mode will be discussed in detail later.

The display image generation unit 102b recognizes a display-related instruction by the user on the basis of the operation content, and controls the display image according to the recognized instruction content.

The display control unit 102b recognizes the gaze direction, recognizes which information among the information being displayed as the display image on the display unit 103 is being focused on, for example, and controls the display image on the basis of the recognized information being focused on.

The display unit 103 displays images on the basis of instructions from the display control unit 102. Specifically, the display unit 103 acts as the projection unit 71, projects image light according to a display image indicated for display by the display control unit 102, and focuses the image onto the user's retina.

The display image generation unit 102b controls the display image to be displayed next according to the display image displayed previously.

<Recognition Procedure for Image Displayed by Information Processing Device of FIG. 1>

A recognition procedure by which the user wearing the above information processing device 31 of FIG. 1 as a wearable device recognizes an image displayed by the information processing device 31 will be described.

Suppose that in the state St1, with respect to a gaze direction as indicated by the dashed line in FIG. 6, an image display area in which a display image is displayed by the information processing device 31 does not exist, and the user wearing the information processing device 31 is directing his or her gaze towards the outside world. Note that FIG. 6 is drawn from a perspective above the user wearing the information processing device 31, in which the arrow indicated by the dashed line indicates the gaze direction, and the image display region P indicates an image made up of a virtual image viewed by the user with image light emitted by the information processing device 31.

Subsequently, for some reason, the state switches the state St1 to the state St2, and the user directs his or her gaze towards the image display region P. At this point, the user's eye is still not focused on the image display region P, and is unable to recognize information in the image display region P.

In the state St2, the user focuses in the gaze direction, and as indicated by the state St3, when the focus point aligns with the image display region P, the user is able to recognize the image display region P.

Additionally, after recognizing the image display region P, in the state St4, the user recognizes the information being displayed in the image display region P.

The user recognizes the image display region P emitted by the information processing device 31 in four steps from the states St1 to St4 described with reference to FIG. 6. In other words, the user wearing the information processing device 31 ordinarily may be said to be switching between the action of looking at the outside world in the state St1 and the action of recognizing the image display region P in the state St4, depending on the situation.

At this point, the user wears the information processing device 31 and looks at the information in the image display region P as necessary while looking at information in the outside world, but when attempting to look at the image display region P in conjunction with an activity such as walking or running, the user looks at the image display region P and reads information with a lowered recognition rate due to the need to look at the outside world during an activity such as walking or running.

For this reason, depending on the user's activity, such as walking or running, and the surrounding environment, in some cases the user may need to look at the image display region P for an extremely short time, and recognize and read the displayed information. In other words, the information displayed in the image display region P may need to be easily recognizable even in an extremely short time, and by making the information easily recognizable in this way, a reduction in the recognition rate due to exercise may be minimized.

<Recognition Rate of Information in Image Displayed by Information Processing Device During Exercise>

FIG. 7 illustrates the recognition rate of information in the image display region P emitted by the information processing device 31 during exercise by the user wearing the information processing device 31, compared among different amounts of exercise, amounts of information, and layouts.

Note that the image display region refers to the region in which a display image viewable together with the visual field of the outside world is displayed by being projected onto the eye with the light guide reflection unit 43, but in the following, the simple term "image display region" will be used to denote the display state in the image display region when a display image is displayed.

In FIG. 7, the display image displayed in the image display region P includes a maximum of four types of information, namely the current time, the distance traveled, the average time per kilometer, and the heart rate, and assuming that at least one of the four types is displayed in the display image, the recognition rates for eight layouts from ID1 to ID8 are compared.

More specifically, in the layout ID1, the current time is displayed centered in the horizontal direction and the vertical direction.

In the layout ID2, the current time and the distance traveled are displayed at a center position in the vertical direction, arranged from left to right in the horizontal direction.

In the layout ID3, the current time and the distance traveled are displayed at a center position in the horizontal direction, arranged from top to bottom in the vertical direction.

In the layout ID4, the distance traveled, the current time, and the average time per kilometer are displayed at a center position in horizontal direction, arranged from top to bottom in the vertical direction.

In the layout ID5, the current time is displayed to the left in the horizontal direction at a center position in the vertical direction, while the distance traveled and the average time per kilometer are displayed to the right in the horizontal direction and arranged from top to bottom in the vertical direction.

In the layout ID6, the current time is displayed on an upper row in the vertical direction and centered in the horizontal direction, while the distance traveled and the average time per kilometer are displayed on a lower row in the vertical direction and arranged from left to right in the horizontal direction.

In the layout ID7, the current time is displayed on an upper row in the vertical direction and centered in the horizontal direction, while the distance traveled, the average time per kilometer, and the heart rate are displayed on a lower row in the vertical direction and arranged from left to right in the horizontal direction.

In the layout ID8, the current time and the distance traveled are displayed on an upper row in the vertical direction and arranged from left to right in the horizontal direction, while the average time per kilometer and the heart rate are displayed on a lower row in the vertical direction and arranged from left to right in the horizontal direction.

In addition, for each of the layouts from ID1 to ID8, FIG. 7 illustrates bar graphs from left to right as the amount of exercise is varied among three types, namely a walk, a slow run, and a fast run.

As illustrated in FIG. 7, for the layouts ID1 to ID3 having two types of information, a good recognition rate is ensured, without changing depending on the amount of exercise.

Also, as indicated by the layouts ID4 to ID8, if three or more types of information are displayed, the reduction in the recognition rate becomes pronounced, and the overall trend is for the recognition rate to drop as the amount of exercise increases.

Furthermore, as indicated by the layouts ID6 and ID7, if three or more types of information are displayed arranged in the vertical direction and arranged in the horizontal direction, the reduction in the recognition rate becomes pronounced. In particular, a large drop in the reduction rate when exercising at a fast run is demonstrated.

From the above, to ensure a good recognition rate irrespective of the amount of exercise, keeping the information displayed simultaneously in the image display region P to two types or less may be considered suitable.

However, since this example only compares arrangements of text information in the horizontal direction and the vertical direction, the amount of information is not necessarily required to be two types.

For example, there is a possibility of improvement by adding changes of color or the like. Also, in cases where the information to present is not text but instead some kind of graphic image or icon, for example, there is a possibility of improvement in the recognition rate.

In any case, however, regarding information whose display is considered necessary, there may be a need to experimentally compute the number of information types that are simultaneously recognizable from among the information that can be displayed at once, such as by varying the layout and colors, and limit the information accordingly.

The following description supposes that for the case of displaying the four types of text-based information in FIG. 7, only up to two types of information are displayed at once as a general rule, and that by switching the classes of information by successive time division for display, a reduction in the recognition rate during exercise may be minimized. However, even if information is presented in groups of some other number depending on the classes of information and the methods of display, a reduction in the recognition rate during exercise may still be minimized.

<Display Control Process by Information Processing Device of FIG. 5>

Accordingly, in the information processing device 31 applying an embodiment of the present technology, only up to two types of information are displayed simultaneously in a single display image displayed in the image display region P, for example, and in the case of displaying a greater number of information types, the number of information types included in a single display image is kept to a certain number for each, and the information is displayed split up over multiple display images by shifting the respective display timings (time-division display). In other words, a certain number of information types are displayed at a time, and as time passes, the information types are switched successively and displayed.

In the following, the term "simultaneous display mode" denotes a display mode that displays multiple information types simultaneously in a single display image, whereas the term "time-division display mode" denotes a display mode that splits up multiple information types by a certain number for display in multiple display images by shifting the respective display timings (time-division display).

In other words, for example, when the total amount of information is three types of information, such as "distance traveled", "current time", and "average time per kilometer", the simultaneous display mode is a display mode in which the three types of "distance traveled", "current time", and "average time per kilometer" are included in a single display image and displayed simultaneously as "3.2 km", "15:01", and "6'05"/km", respectively, as indicated by the image display region PA in the left part of FIG. 8, and as time passes, display images presenting changed information are successively switched one at a time and displayed (displayed in a time series). In other words, in the case of the simultaneous display mode, display images presenting these three types of information simultaneously are successively displayed while varying the information as time passes.

On the other hand, when displaying three types of information such as "distance traveled", "current time", and "average time per kilometer" not with the simultaneous display mode but instead with the time-division display mode, as the time passes over times t1, t2, t3, and so on, at the first timing at the time t1, "3.2 km" is displayed as the "distance traveled", as indicated by the display image in the image display region Pa in the right part of FIG. 8, while at the next timing at the time t2, "15:01" is displayed as the "current time", as indicated by the display image in the image display region Pb, and at the next timing at the time t3, "6'05"/km" is displayed as the "average time per kilometer", as indicated by the display image in the image display region Pc, with the above display images being displayed in order as time passes (displayed by time division). In other words, in the case of the time-division display mode, three types of display images, namely the image display regions Pa, Pb, and Pc, are displayed at respectively shifted timings, and in addition, the information that changes as time passes is displayed repeatedly, three images at a time (displayed by time division and in a time series).

In other words, in the case of the time-division display mode, among the three types of display images, namely the image display regions Pa, Pb, and Pc, the display image to be displayed is set by switching with shifted timings, so that at each timing, a display image of the information to be displayed is displayed, while display images other than the display image of the information to be displayed are not displayed. Furthermore, the display is switched as time passes (in a time series) in units of the three types of display images, namely the image display regions Pa, Pb, and Pc.

In other words, the display images displayed in the image display regions Pa, Pb, and Pc are a first display image to a third display image, and in the case of supposing that the timings at which to change in the time direction are the times t11, t12, and t13, with the time division display mode, at the timing of the time t11, for example, the first display image is set as the display image to be displayed, and the display enters a state in which the first display image is displayed, whereas the second and third display images are not displayed. Next, at the timing of the time t12, the second display image is set as the display image to be displayed, and the display enters a state in which the second display image is displayed, whereas the first and third display images are not displayed. Furthermore, at the timing of the time t13, the third display image is set as the display image to be displayed, and the third display image is displayed, whereas the first and second display images are not displayed.

Additionally, by repeating the operation from the time t11 to the time t13 as time passes, the three types of display images are displayed in a time series.

Note that when the three types of display images are a first image, a second image, and a third image, the three images may not only be displayed repeatedly one at a time in a fixed order in units of "first image, second image, third image", such as in the order of the first image, the second image, the third image, the first image, the second image, the third image, and so on, but may also be displayed two or more times within a repeating unit, as long as the three types of display images are used. For example, the three images may also be displayed repeatedly in units of "first image, second image, third image, second image, third image", such as in the order of the first image, the second image, the third image, the second image, the third image, the first image, the second image, the third image, the second image, the third image, and so on.

According to such a process, the recognition rate is guaranteed by limiting the number of information types displayed in a single display image displayed in the image display region, while in addition, when displaying a number of information types greater than the limited number, the information types are split up over multiple display images and given respectively shifted timings (different timings) for display (that is, displayed by time division), thereby making it possible to minimize a reduction in the recognition rate during exercise.

In other words, the information processing device 31 of FIG. 5 executes a display control process that, for up to two types of information, uses the simultaneous display mode that displays information simultaneously in a single display image, whereas for more types of information, uses the time-division display mode, in which all information types are successively split up into information that is less than the number of recognizable information types in a single display image, and the multiple display images respectively presenting the split-up number of information types are switched and displayed at different timings (with respectively shifted timings). Accordingly, at this point, the display control process by the information processing device 31 of FIG. 5 will be described with reference to the flowchart in FIG. 9.

Also, this embodiment describes an example in which up to two information types are displayed simultaneously in the simultaneous display mode, whereas for more types of information, one type of information at a time is displayed in the time-division display mode. However, if the number of simultaneously recognizable information types is a certain number equal to or greater than two, the simultaneous display mode may also be configured display the certain number of simultaneously recognizable information types in a single display image simultaneously, and switch the display as time passes (that is, display the display images one at a time in a time series).

On the other hand, if the number of information types exceeds the certain number of simultaneously recognizable information types, the time-division display mode may also be configured to display multiple display images presenting information split up into the number of simultaneously recognizable information types or a smaller number with respectively shifted timings, and display the information while switching in units of the multiple display images as time passes (that is, display the multiple display images by time division and in a time series).

Namely, in step S11, the mode determination unit 102a of the display control unit 102 initializes a counter n for counting a sequence of images to be displayed in a time series on the display unit 103 as the image display region P.

In step S12, the mode determination unit 102*a* controls the activity state information acquisition unit 101 to acquire activity state information, or in other words, information about speed as the exercise intensity, for example, thereby acquires the movement speed of the user wearing the information processing device 31, and determines whether or not the movement speed is greater than a certain speed v0.

Herein, the speed v0 is taken to be a speed of 0 indicating a stopped state, or a speed close to a stopped state extremely close to a speed of 0, for example. In other words, in step S12, it is determined whether or not the user's movement speed is a speed of 0, or in other words, whether or not the user's exercise intensity is completely 0.

As discussed earlier, the exercise intensity indicates the strenuousness of the user's activity. In this example, speed is used as the activity state information, and thus as the speed becomes faster, the exercise intensity becomes stronger (higher), and at this point, the amount of information the user is able to recognize simultaneously when looking at a single image display region decreases, and the recognition rate falls. Conversely, as the activity state information, namely the speed, becomes slower, the exercise intensity becomes weaker (lower), the amount of information the user is able to recognize simultaneously when looking at a single image display region increases, and the recognition rate rises.

In addition, when using factors such as the amount of vibration, the amount of exercise, or the heart rate as the activity state information, as the vibrations become more intense, as the amount of exercise becomes greater, and as the heart rate rises, the exercise intensity becomes stronger, and the recognition rate falls. Conversely, as the activity state information, namely the vibrations become smaller, as the amount of exercise becomes smaller, and as the heart rate falls, the exercise intensity becomes weaker, and the recognition rate rises.

Consequently, since the exercise intensity is set according to the activity state information, and the recognition rate varies according to the exercise intensity, a display mode, such as the simultaneous display mode or the time-division display mode, is switched according to the activity state information, or in other words, according to the exercise intensity.

In step S12, if the user's movement speed is less than the speed v0 and treated as being a stopped state, or in other words, if the exercise intensity is 0, the process proceeds to step S16.

In step S16, the mode determination unit 102*a* sets the display mode to the simultaneous display mode, and supplies the display mode setting to the display image generation unit 102*b*.

In step S17, the display image generation unit 102*b* generates a display image presenting all displayable information simultaneously, and controls the display unit 103 to display the display image. In other words, in this case, the exercise intensity based on the activity state information is weak and the user is barely moving at all, or in other words, the user is treated as standing still, for example. Thus, the user is judged to be capable of recognizing more information, and an image is displayed in which the four types of displayable information, such as those corresponding to the layout ID8 in FIG. 7, for example, are all displayed.

On the other hand, in step S12, if the speed is greater than the speed v0 and treated as at least not a stopped state, the process proceeds to step S13.

In step S13, the mode determination unit 102*a* determines whether or not a display switching mode is active. In other words, herein, the display switching mode refers to a mode that switches the display according to the amount of exercise (exercise intensity) irrespectively of the intent of the user wearing the information processing device 31, switching to the simultaneous display mode that displays all information simultaneously when the exercise intensity is greater than 0 but less than a certain value, and switching to time-division display mode that automatically decreases the amount of information to display and displays information successively by time division when the exercise intensity becomes greater than the certain value. Note that in the flowchart in FIG. 9, if the display switching mode is not active (if the display switching mode is not on), the display mode is constantly set to the simultaneous display mode irrespective of the exercise intensity, but another configuration may allow the display mode setting to be locked to either the simultaneous display mode or the time-division display mode irrespective of the exercise intensity.

In step S13, if the display switching mode is not active, the process proceeds to step S14.

In step S14, the mode determination unit 102*a* controls the display unit 103 to display an image asking whether or not to turn on the display switching mode.

In step S15, the mode determination unit 102*a* determines, on the basis of information from the operating unit 104, whether or not the operating unit 41*a* was operated and an operation turning on the display switching mode is performed. For example, if an operation turning on the display switching mode is not performed, the process proceeds to steps S16 and S17. In other words, in this case, the display mode is set to the simultaneous display mode irrespective of the activity state, and images that present all information constantly continue to be displayed.

On the other hand, in step S15, if the operating unit 41*a* is operated and the display switching mode is treated as being turned on, or if the display switching mode is on in step S13, the process proceeds to step S18.

In step S18, the mode determination unit 102*a* sets the display mode to the time-division display mode, and supplies the display mode setting to the display image generation unit 102*b*.

In step S19, the mode determination unit 102*a* determines whether or not the gaze direction supplied by the gaze detection unit 106 has been fixed in a specific direction for a certain amount of time or more. In step S19, in the case of determining that the gaze direction has not been fixed in a specific direction for a certain amount of time or more, the process proceeds to step S20.

In step S20, the mode determination unit 102*a* determines whether or not the movement speed obtained as the activity state information acquired by the activity state information acquisition unit 101 is equal to or greater than a speed v1 (where v1>v0) of approximately walking speed. In step S20, it is determined whether or not the user's movement speed is equal to or greater than walking speed, namely the speed v1 (for example, if the user's movement speed is approximately the speed of a slow run). In step S20, if the user appears to be moving at a movement speed that is equal to or greater than the speed v1 (for example, if the user's movement speed is approximately the speed of a slow run), the process proceeds to step S21.

In step S21, the display image generation unit 102*b* determines whether or not a certain time t1 has passed since the last timing when an image was displayed, and repeats a similar process until the time t1 passes. Subsequently, after the certain time t1 has passed since the last timing when an image was displayed, the process proceeds to step S23.

In addition, in step S20, if the movement speed is not equal to or greater than the speed v1, and the user is judged to be moving at approximately the speed of walking, for example, the process proceeds to step S22.

In step S22, the display image generation unit 102b determines whether or not a certain time t2 (where t2<t1) has passed since the last timing when an image was displayed, and repeats a similar process until the time t2 passes. Subsequently, after the certain time t2 has passed since the last timing when an image was displayed, the process proceeds to step S23.

In step S23, the display image generation unit 102b determines whether or not an interrupt display image exists. In other words, as the exercise intensity, namely the user's movement speed, becomes faster, the amount of information that can be recognized tends to decrease. Thus, at this point, although the display mode is the time-division display mode that successively switches and displays images containing respective amounts of information that can be recognized at once, it is determined whether or not there exists an interrupt display image to be displayed in addition to the images continually displayed successively in a time series, even by interrupting with a particularly relevant image, only when approaching a feature such as turn or an intersection as part of route navigation or the like, for example.

In step S23, if an interrupt display image does not exist, the process proceeds to step S24.

In step S24, the display image generation unit 102b reads out image format information stored in the storage unit 105, generates an image containing the information to be displayed in the nth place from among the images to be displayed by switching in a time series, and causes the display unit 103 to display the generated image.

In step S25, the display image generation unit 102b determines whether or not the counter n has reached a maximum value, and if not the maximum value, increments the counter n by 1 in step S26. Also, in step S25, if the counter n is judged to have reached the maximum value, the counter n is reset to 0 in step S27.

In step S28, the mode determination unit 102a determines whether or not the process has ended, and if not ended, the process returns to step S12. Also, in step S28, in the case of judging that the process has ended, the process ends.

In other words, between the case in which the movement speed is a walking speed and the case in which the movement speed is faster than walking speed, such as a running speed, for example, it becomes possible to switch the display switching time for images to be displayed by switching in a time series, so that for the case in which the movement speed is a running speed, since the recognition rate is lower than when moving at a walking speed, the display time during which the same image is displayed may be switched to become longer as the movement speed rises.

As a result, as the movement speed rises, the time during which the same image is displayed becomes longer to the extent that the recognition rate falls, thereby making it possible to decrease the reduction in the recognition rate by using the display time to compensate for the recognition rate that falls according to the movement speed. Also, likewise in this case, the information to be displayed successively is displayed so that two types change at a time, for example, thereby making it possible to display information while minimizing the reduction in recognition rate, even for information for which the recognition rate would fall if four types or the like were displayed all at once.

Meanwhile, in step S21, if an interrupt display image exists, the process proceeds to step S27.

In step S27, the display control unit 102 reads out image information stored in the storage unit 105, generates a relevant interrupt display image, and causes the display unit 103 to display the generated interrupt display image.

In other words, in addition to the information to be displayed in a time series, it becomes possible to display an interrupt display image as needed. In this case, it becomes possible to display, at appropriate timings, interrupt display images to be displayed at appropriate timings, while also minimizing a reduction in the visual recognition rate according to the user's movement speed.

Note that the information to be displayed in a time series is information such as the movement speed, the distance traveled, the current time, and the average speed per kilometer, for example, and is information that changes from moment to moment as time passes. However, since the amount of information that is recognizable in a single display image changes according to the user's exercise intensity, even the information displayed in a time series is displayed in the simultaneous display mode in some cases, and displayed in the time-division display mode in other cases.

In the case of the simultaneous display mode, multiple types of information are displayed simultaneously, as indicated by the image display region PA in the left part of FIG. 8, for example, and as long as an interrupt display image does not exist, the information that changes from moment to moment will be displayed continually at time intervals according to the exercise intensity as a general rule. In contrast, in the case of the time-division display mode, multiple types of information are displayed individually in the order of the image display regions Pa, Pb, and Pc in the right part of FIG. 8, for example, and as long as an interrupt display image does not exist, the information will be switched and displayed continually at time intervals according to the exercise intensity as a general rule. In this case, the three images of the image display regions Pa, Pb, and Pc are respectively displayed while being switched at time intervals according to the exercise intensity, while in addition, the three types of information displayed in this three-image set are repeatedly displayed continually while changing the information as time passes.

Furthermore, unlike such time series information, the interrupt display image is an image displayed only when a specific condition is met, such as guide display information to be displayed only at a timing of approaching an intersection or the like as part of navigation or the like, for example, and thus is information different from the information that is repeatedly displayed in a time series.

Furthermore, in step S19, if the gaze direction has been fixed in a certain direction for a certain amount of time or more, the process proceeds to step S30.

In step S30, the display image generation unit 102b generates an image that selectively displays the information displayed in the gaze direction, and causes the display unit 103 to display the generated image.

In other words, in the case of displaying all information, for example, when four types of information made up of the time, the distance traveled, the average time per kilometer, and the heart rate are displayed as indicated by the layout ID8 in FIG. 7, if the gaze direction becomes fixed for a certain amount of time or more in the display region of the distance traveled indicated in the upper-right part of the region in which the image display region P is displayed, the user's intent is taken to be a desire to display information about the distance traveled, and the information about the distance traveled is displayed.

According to such operation, regarding currently-displayed information that changes in a time series about which the user wants to know, by fixing one's gaze direction in a position corresponding to the display position of that information, it is possible to prompt the information processing device 31 to display that information, and in response to the request, it is possible to display an image desired for display according to the user's request.

The movement speed v1 that acts as a threshold value in step S20 may also be switched dynamically according to factors such as the activity state information.

<First Example of Application Used when Running>

According to the process described with reference to the flowchart in FIG. 9, in the case of an application used when running, for example, images like those illustrated in FIG. 10 are displayed successively.

In other words, for the image display region P displayed by the display unit 103, as indicated by the image display region P1 in FIG. 10, the movement speed is displayed on a top row, the running duration is displayed on a bottom row, and the line extending horizontally to divide the two types of information is treated as a gauge indicating the current position with respect to the entire route (color is added according to the distance traveled). The image display region P2 illustrates information that guides (navigates) the user along the route set as the course to run. The image display regions P3, P5, P6, P8, and P9 are information in which the movement speed and the duration indicated by the image display region P1 are successively switched and displayed in a time series (continuously displayed as time passes). The image display region P4 displays "Speed Up", and is an image encouraging the user to run faster because the current movement speed is lower than a speed set as the running speed. The image display region P7 is an image encouraging the user to keep running in the same way, since the current movement speed has reached the set speed.

In other words, according to the above process, after movement speed, the duration, and information about the current position with respect to the entire route when starting out is displayed in the image display region P1, the image display region P2 is displayed as an interrupt display image at the next timing. Consequently, the user is able to check the route to run. Subsequently, the movement speed, the duration, and information about the current position with respect to the entire route which are displayed repeatedly in a time series are displayed by the image display region P3. At this point, since the movement speed is lower than the set speed, the image display region P4 is displayed as an interrupt display image. After that, the image display regions P5 and P6 are displayed successively in a time series, by which the movement speed, the duration, and information about the current position with respect to the entire route are displayed. At this point, the set speed is reached, and thus the image display region P7 is displayed as an interrupt display image, by which information encouraging the user to keep moving at the current speed is displayed. Subsequently, the image display regions P8 and P9 are displayed successively in a time series, by which the movement speed, the duration, and information about the current position with respect to the entire route are displayed.

In this case, the time during which the image display regions P1 to P9 are successively displayed becomes longer as the movement speed becomes faster, thereby making it possible to minimize a reduction in the recognition rate according to the movement speed. Also, regarding the information being displayed in a time series, the information that changes from moment to moment as time passes, as opposed to the slowly-changing information about the current position with respect to the entire route, is the two types of information of the movement speed and the duration, thereby making it possible to minimize a reduction in the recognition rate like that illustrated in FIG. 7. Furthermore, information relevant at respective timings depending on the situation is displayed at appropriate timings as interrupt display images such as the image display regions P4 and P7, thereby making it possible to display appropriate information at appropriate timings.

<First Example of Application Used when Cycling>

In addition, according to the process described with reference to the flowchart in FIG. 9, in the case of an application used when cycling, for example, images like those illustrated in FIG. 11 are displayed successively.

For the image display region P displayed by the display unit 103, first, as indicated by the image display region P21 in FIG. 11, a graphical map is displayed, the entirety of the upcoming route is displayed, and a compass-shaped icon indicating the forward direction at the current position is displayed. The image display region P22 is an enlarged display of the route near the current position. The image display region P23 displays an enlarged view of the nearby route in the left part, and in the right part, indicates "12%" as the gradient at the current position. The image display regions P24 and P25 display an enlarged view of the route near the current position in the left part, and in the right part, indicate "35 km/h" and "10 km/h", respectively, as the current movement speed.

The image display regions P26 and P27 are graphical images indicating that a right turn is required on the route. The image display region P28 is an image displaying the names of mountains (Mt. Garan, Mt. Daruma) which act as landmarks on the route.

The image display regions P29 and P30 display an enlarged view of the route near the current position in the left part, and in the right part, indicate that the movement speed is "1 km/h" and "19 km/h", respectively. The image display region P31 displays the entire route, and displays a compass-shaped icon indicating the forward direction at the current position.

Herein, images of the entire route and enlarged display images of the route near the current position, as indicated by the image display regions P21 and P22, as well as images that display an enlarged view of the route near the current position in the left part and display the movement speed in the right part, as indicated by the image display regions P24, P25, P29, and P30, may be displayed successively and repeatedly in a time series, whereas all other images may be treated as interrupt display images.

As a result, after the image of the entire route is displayed by the image display region P21, next, an enlarged image of the route near the current position is displayed by the image display region P22. At this point, if information indicating a gradient is detected in the activity state information, the image display region P23, which displays an enlarged image of the route near the current position in the left part and indicates that the gradient at the current position is "12%" in the right part, is displayed as an interrupt display image.

After that, the image display regions P24 and P25 are displayed in a time series, and at the timing of making a right turn, images encouraging the user to make a right turn, as indicated by the image display regions P26 to P28, are displayed as interrupt display images. At this point, the names of mountains that act as landmarks are displayed after a certain time passes from when the image encouraging the user to make a right turn was displayed. As a result, it is possible to enable the user to recognize important information, such as making a right turn, and after that, enable the user to recognize the names of mountains that act as landmarks. After that, images are displayed in a time series again by the image display regions P29 to P31.

With such a display, the display time of each image likewise becomes longer as the movement speed becomes faster, and thus a reduction in the recognition rate may be decreased. Also, since a maximum of two types of information are displayed simultaneously, a reduction in the recognition rate may be decreased. Furthermore, regarding information relevant at respective timings depending on the situation, interrupt display images are displayed at appropriate timings, thereby making it possible to display appropriate information.

<First Example of Application Used when Playing Tennis>

Furthermore, according to the process described with reference to the flowchart in FIG. 9, in the case of an application used when playing tennis, for example, images like those illustrated in FIG. 12 are displayed successively. Note that the activity state information in this case is information about a pressure distribution on the racquet face of a tennis racquet used by the user, and an image depicting the rotation of a tennis ball.

For the image display region P displayed by the display unit 103, first, as indicated by the image display region P51, the position on the racquet face as well as the pressure distribution when the tennis ball hits the racquet during a serve are indicated.

Next, at the timing of returning the ball, as indicated by the image display region P52, the position where the ball was returned on the racquet face is indicated. Subsequently, at the next timing, as indicated by the image display region P53, the speed of the returned ball (in the drawing, 102 km/h) and the level of spin (in the drawing, +3 spin) are displayed.

Thereafter, a similar process is repeated, and at the timing of returning the ball again, as indicated by the image display region P54, the position where the ball was returned on the racquet face is indicated. Subsequently, at the next timing, as indicated by the image display region P55, the speed of the returned ball (in the drawing, 72 km/h) and the level of spin (in the drawing, +1 spin) are displayed.

Subsequently, when the next serve is played, as indicated by the image display region P56, the position on the racquet face as well as the pressure distribution when the ball hits the racquet during the serve are indicated.

In other words, while strokes are repeated in this way, the image display regions P52, P53, P54, and P55 are repeatedly displayed in a time series, while the image display regions P51 and P56 during a serve are displayed as interrupt display images.

With such a display, the display time of each image likewise becomes longer as the movement speed becomes faster, and thus a reduction in the recognition rate may be decreased. Also, since a maximum of two types of information are displayed simultaneously, a reduction in the recognition rate may be decreased. Furthermore, information relevant at respective timings depending on the situation is displayed at appropriate timings as interrupt display images, thereby making it possible to present appropriate information.

<First Example of Application Used when Playing Golf>

In addition, according to the process described with reference to the flowchart in FIG. 9, in the case of an application used when playing golf, for example, images like those illustrated in FIG. 13 are displayed successively. Note that the activity state information in this case is the user's position on the golf course, the course layout of the golf course, and the wind speed.

For the image display region P displayed by the display unit 103, first, as indicated by the image display region P71, the distance from the user's current position to a center position of the green (displayed as 167 yd in the drawing) and the distance to the edge of the green (displayed as 155 yd in the drawing) are displayed.

Next, as indicated by the image display region P72, the distance from the user's current position to the center position of the green (displayed as 165 yd in the drawing) and the distance to the edge of the green (displayed as 153 yd in the drawing) are displayed.

Next, as indicated by the image display region P73, the 7 iron (displayed as 71 in the drawing) is indicated as being the recommended club for the approach from the current position given the course layout.

Furthermore, as indicated by the image display region P74, the layout around the green is displayed more specifically by graphics, while in addition, the position of the hole on the green in the is displayed graphically as distances from the edges of the green. More specifically, in the drawing, provided that the upward direction on the layout is the northern direction, the distance from the eastern edge to the hole is indicated as 8 yd, while the distance from the southern edge to the hole is indicated as 30 yd.

Next, as indicated by the image display region P75, the wind speed and direction of wind on the green is indicated, and in the drawing is indicated as a north-northwest wind having a speed of 8 m/s.

Next, as indicated by the image display region P76, the distance from the user's current position to the hole (displayed as 162 yd in the drawing) is displayed.

Thereafter, the image display regions P77 to P79 are displayed similarly to the image display regions P71 to P73.

In other words, in this example, like the image display regions P71 to P76, an image displaying the distance from the user's position to the center of the green and the distance to the green edge, an image displaying the recommended type of club, an image of the layout on the green, an image displaying the wind speed and wind direction, and an image displaying the distance from the user to the hole are displayed successively in a time series.

With such a display, the display time of each image likewise becomes longer as the movement speed becomes faster, and thus a reduction in the recognition rate may be decreased. Also, since a maximum of a certain number of types of information (in this embodiment, two types) are displayed simultaneously, a reduction in the recognition rate may be decreased, while also displaying more information by switching to enable recognition.

Note that the above describes examples that enable easier recognition of more information while also decreasing a reduction in the recognition rate by switching between a simultaneous display mode and a time-division display mode for information to be displayed in a time series and information to be displayed as interrupt display images, depending on activity state information, namely the exercise intensity.

In addition, regarding display images displayed in the image display region, the display time is configured to be switched according to the movement speed, but the display time may also be switched according to factors other than the movement speed. For example, the time allocated for the display of information displayed in the image display region may be switched according to the condition by which the information is displayed, or the importance of the information. For example, information such as instructions to take emergency avoidance action due to the occurrence of a disaster or an accident may be processed to have a longer display time or the like.

Furthermore, the length of the display time may also be set according to an exercise intensity other than the movement speed, and may be varied according to factors such as vibration, gaze, heart rate, body temperature, amount of perspiration, brain waves, or myoelectric potential, for example. In such cases, if the exercise intensity becomes stronger, the recognition rate is considered to fall and the display time may be lengthened, whereas if the exercise intensity becomes weaker, the drop in the recognition rate is considered to be small, and the display time may be shortened.

Also, in the case of setting the length of the display time according to the exercise intensity, the threshold value for switching the length of the display time may also be varied according to the situation. In other words, the process discussed above describes an example of switching the display time according to whether or not the movement speed is greater than the speed v1, but the display time may also be varied according to conditions such as the class of information being displayed in the display images, the exercise intensity, or the application.

Second Embodiment

The foregoing describes an example in which, when the user's exercise intensity is small, all information is displayed in the simultaneous display mode, whereas when the user's exercise intensity is large and there is too much displayed information to recognize simultaneously, the information is split up into a number of information types for which the recognition rate can be maintained at a glance, and displayed by being switched successively, thereby presenting information to the user without lowering the recognition rate, even if there is a large amount of information.

However, regarding features such as the class of displayed information, once a person memorizes the position of the information, he or she recognizes the class of information in association with the position, and thus the recognition rate is unaffected even if the information is displayed with the units or label omitted.

In other words, as illustrated in FIG. 14, when displaying the overall average travel time per kilometer in an upper row and the current travel time per kilometer in a lower row of the same image, with regard to the display of labels such as "Current" and "Average" displayed in front of the numerical values indicating the actual information, or the display of units such as "min/km" displayed behind, the recognition rate is relatively unaffected even if such labels or units are displayed smaller or even omitted.

More specifically, even in the case of a small display as illustrated in the left part of FIG. 14, the case of a small display of just the units as illustrated in the center part of FIG. 14, or the case of omitting the display in front and presenting a small display behind as illustrated in the right part of FIG. 14, the recognition rate is still roughly 90%, indicating that the recognition rate is unaffected.

In other words, by omitting unchanging information such as labels and units from display according to the movement speed, and displaying only the changing information that is substantially relevant, a reduction in the recognition rate may be minimized.

<Configuration of Second Embodiment of Information Processing Device>

Next, FIG. 15 will be referenced to describe an example configuration of a second embodiment of the information processing device 31, which is configured to omit the display of information whose display content does not change, such as labels and units, according to the movement speed. Note that in the information processing device 31 of FIG. 15, components equipped with the same functions as components in the information processing device 31 of FIG. 5 are denoted using the same names and the same signs, respectively, and the description of such components may be reduced or omitted where appropriate.

Namely, the information processing device 31 of FIG. 15 differs from the information processing device 31 of FIG. 5 in that a display control unit 121 is provided instead of the display control unit 102. The basic function of the display control unit 121 is similar to the display control unit 102, but as the movement speed becomes faster, the display control unit 121 switches to a display mode that omits the display of information that does not change after being displayed once, such as labels and units attached to information.

More specifically, the display control unit 121 is equipped with a mode determination unit 121a and a display image generation unit 121b. The basic operation of the mode determination unit 121a is similar to the mode determination unit 102a, but as discussed above, the mode determination unit 121a switches the display mode to omit the display of information that does not change after being displayed once, such as labels and units. In other words, in this example, the display is switched among four types of display modes: the simultaneous display mode and the time-division display mode, as well as a simultaneous abbreviated display mode and a time-division abbreviated display mode that do not display information with unchanging display content.

In addition, herein, information with unchanging display content refers to information including unchanging information that is not linked to changes in exercise intensity detected as the activity state information, as well as labels or units, for example.

However, regarding the units or labels of information such as the distance traveled, in which the information is displayed in units of meters (m) in the time period immediately after the start, and displayed is units of kilometers (km) after the distance exceeds 1000 m, or information such as the elapsed time, in which the information is displayed in minutes at first but then displayed in units of hours after exceeding 60 min, such units or labels may also be treated as information with unchanging display content as long as the display does not change.

Consequently, the information with unchanging display content referred to herein may be, if units of length, a unit such as "m" under the condition of being from 0 m to 999 m or "km" under the condition of exceeding 1000 m, or if a unit of speed, a unit such as "m/s" under the condition of being from 0 m/s to 999 m/s or "km/s" under the condition of exceeding 1000 m, or if a unit of time, a unit such as "min" under the condition of being from 0 min to 59 min or "h" under the condition of exceeding 60 min, or the like. Thus, information with unchanging display content referred to herein includes information such as units and labels that do not change under certain conditions.

In other words, even if a unit or label changes, insofar as the unit or label does not change under a certain condition, that unit or label is treated as information with unchanging display content under the certain condition. Note that the display image generation unit 121b is equipped with the same function as the display image generation unit 102b.

<Display Control Process by Information Processing Device of FIG. 15>

Next, the flowcharts in FIGS. 16 and 17 will be referenced to describe a display control process by the information processing device 31 of FIG. 15. Note that the processing in steps S41 to S45, S47, S48, S51 to S55, step S57, steps S60 to S63, S65, and S69 in the flowcharts in FIGS. 16 and 17 is similar to the processing in steps S11 to S24, and steps S25 to S30 in FIG. 9, and thus description thereof will be reduced or omitted.

In other words, if the display switching mode is not active according to the processing from steps S41 to S45, in step S46 (FIG. 16), the mode determination unit 121a determines whether or not the display in the simultaneous display mode has continued for a certain amount of time. If the display switching mode is not active, in the initial processing, the display in the simultaneous display mode has not continued for a certain period of time, and thus a display image presenting all information simultaneously is displayed in the simultaneous display mode according to the processing of steps S47 and S48.

If the state of the display switching mode being inactive continues, the display in the simultaneous display mode is continued, thereby causing the processing of step S46 to be repeated, and when the duration in the simultaneous display mode reaches the certain amount of time, the process proceeds to step S49.

In step S49, the mode determination unit 121a sets the display mode to the simultaneous abbreviated display mode, and supplies the display mode setting to the display image generation unit 121b.

In step S50, the display image generation unit 121b switches to an abbreviated display that displays all displayable information simultaneously, while also reducing the size of or omitting information such as labels and units that the user has likely memorized and does not need to look at anymore, since such information has been displayed continually without change for a certain amount of time.

The display image generation unit 121b generates a display image, and controls the display unit 103 to display the display image. In other words, since a certain amount of time has elapsed in the state of all information being displayed, in this case, since the user is in a state allowing for the recognition more information, and since features such as the units and label of each information type have been displayed continually, the user is assumed to have memorized such features, and thus a display image presenting all information but with the units omitted is generated and made to be displayed on the display unit 103.

For example, in the case of displaying "current time", "distance traveled", "average time per kilometer" and "heart rate", in the simultaneous display mode, as indicated by the image display region P91 in FIG. 18, the units are not indicated for the current time, but "km" is displayed as the units of "distance traveled", "/km" is displayed as the units of "average time per kilometer", and "bpm" is displayed as the units of "heart rate". In contrast, in the simultaneous abbreviated display mode, as indicated by the image display region P92 in FIG. 18, "km" as the units of "distance traveled", "/km" as the units of "average time per kilometer", and "bpm" as the units of "heart rate" are all omitted.

In this way, by displaying in the simultaneous display mode, all information with the classes of information already recognized is displayed in the user's field of vision, thereby making it possible to minimize a reduction in the recognition rate of the information to display. Additionally, after the information is displayed for a certain amount of time in the simultaneous display mode, in a situation in which the user is likely to have memorized the units and labels, the units and labels are not displayed, thereby making it easier to recognize the actual numerical values.

In addition, according to the processing from step S41 to S55, if the gaze direction is not fixed and a display is presented while a time t1 or t2 elapses from the previous display time, or in other words, if there is no interrupt display, the process proceeds to step S57 (FIG. 17).

In step S57, the mode determination unit 121a determines whether or not the user's current movement speed supplied by the activity state information acquisition unit 101 is faster than a certain speed v2, and if faster, the process proceeds to step S59. The speed v2 is faster than the speed v1. Consequently, being faster than the speed v2 indicates, in the assumed case of running, for example, a state of a particularly fast run.

In step S59, the mode determination unit 121a switches the display mode setting from the time-division display mode to the time-division abbreviated display mode, and supplies the display mode setting to the display image generation unit 121b.

In step S60, the display image generation unit 121b reads out image format information stored in the storage unit 105, generates an image containing the information to be displayed in the nth place from among the images to be displayed by switching in a time series, additionally omits features such as labels and units, and causes the display unit 103 to display the generated image.

In other words, moving at particularly high speed may be said to be a state in which the recognition rate falls particularly easily. Accordingly, in such cases, the display is switched to an abbreviated display that reduces the size of or omits information such as labels and units which was already displayed at low speed and which the user has likely memorized and does not need to look at anymore. In this way, only a minimum necessary level of information is displayed with the classes of information already recognized in the user's field of vision, thereby making it possible to minimize a reduction in the recognition rate of the information to display.

Additionally, at this point, in step S57, if the current movement speed is slower than the speed v2, in step S58, the display image generation unit 121b reads out image format information stored in the storage unit 105, generates an image containing the information to be displayed in the nth place from among the images to be displayed by switching in a time series, and displays, on the display unit 103, the generated image which includes the usual labels and units.

Furthermore, in step S56, if interrupt display information exists, the process proceeds to step S65.

In step S65, the mode determination unit 121a determines whether or not the user's current movement speed supplied by the activity state information acquisition unit 101 is faster than the certain speed v2, and if faster, the process proceeds to step S67.

In step S67, the mode determination unit 121a switches the display mode setting from the time-division display mode to the time-division abbreviated display mode, and supplies the display mode setting to the display image generation unit 121b.

In step S68, the display image generation unit 121b reads out image information stored in the storage unit 105, generates a relevant interrupt display image, additionally omits features such as labels and units, and causes the display unit 103 to display the generated interrupt display image.

In other words, even in the case in which an interrupt display image exists, by displaying only a minimum necessary level of information with the classes of information already recognized, it is possible to minimize a reduction in the recognition rate of the information to display.

On the other hand, in step S61, if the movement speed is slower than the speed v2, in step S62, the display image generation unit 121b reads out image format information stored in the storage unit 105, generates a relevant interrupt display image, and causes the display unit 103 to display the interrupt display image which includes the usual labels and units.

Furthermore, in step S51, if the gaze direction has been fixed for a certain amount of time or more, the process proceeds to step S69.

In step S69, the mode determination unit 121a determines whether or not the user's current movement speed supplied by the activity state information acquisition unit 101 is faster than the certain speed v2, and if faster, the process proceeds to step S71.

In step S71, the mode determination unit 121a switches the display mode setting from the time-division display mode to the time-division abbreviated display mode, and supplies the display mode setting to the display image generation unit 121b.

In step S72, the display image generation unit 121b generates an image that selectively displays the information displayed in the gaze direction, additionally omits features such as labels and units, and causes the display unit 103 to display the generated image.

In other words, even in the case of displaying an image of the information in the gaze direction, by displaying only a minimum necessary level of information with the classes of information already recognized, it is possible to minimize a reduction in the recognition rate of the information to display.

On the other hand, in step 365, if the movement speed is slower than the speed v2, in step S66, the display image generation unit 121b generates an image selectively displaying the information displayed in the gaze direction, and causes the display unit 103 to display the generated image which includes the usual labels and units.

Although the foregoing describes an example of omitting features such as labels and units from display according to the movement speed, the information with changing display content may also be displayed larger or be made to blink so as to emphasize the display and make such information easier to recognize than features such as the labels and units. Alternatively, both the abbreviated display and the emphasizing display may be executed.

<Second Example of Application Used when Running>

In other words, according to the process described with reference to the flowcharts in FIGS. 16 and 17, in the case of the application used when running as discussed earlier, for example, at low speeds, images like those illustrated in FIG. 10 are successively displayed, whereas at high speeds, the display of units such as "km/h" is omitted, as indicated by the image display regions P103, P105, P106, and P108 in FIG. 19. Note that the image display regions P101 to P109 in FIG. 19 correspond to the image display regions P1 to P9 in FIG. 10.

<Second Example of Application Used when Cycling>

In addition, according to the process described with reference to the flowcharts in FIGS. 16 and 17, for the case of an application used when cycling, for example, when the movement speed is fast, the entirety of the route is displayed as indicated by the image display region P121 in FIG. 20, whereas at low speeds, a zoomed-in view of just the route near the current position is displayed, and in addition as indicated by the image display region P122, and in addition, a scale in units of 1 km is displayed as illustrated in the right part of the drawing. Furthermore, at low speeds, a zoomed-in view of just the nearby route is displayed together with the current speed, as indicated by the image display region P123, and when a high speed is reached again, the speed is omitted from display, as indicated by the image display region P124.

<Second Example of Application Used when Playing Tennis>

Furthermore, according to the process described with reference to the flowcharts in FIGS. 16 and 17, for the case of an application used when playing tennis, for example, when a rally goes back and forth slowly and the user's movement speed is low, units such as the units "km/h" for the speed of the ball and "spin" displayed as the units of spin for the ball are displayed, as indicated by the image display region P141 in FIG. 21. In contrast, for example, when a rally goes back and forth quickly and the user's movement speed is high, units such as the units "km/h" for the speed of the ball and "spin" displayed as the units of spin for the ball are omitted from the display, as indicated by the image display region P142 in FIG. 21.

<Second Example of Application Used when Playing Golf>

In addition, according to the process described with reference to the flowcharts in FIGS. 16 and 17, for the case of an application used when playing golf, for example, when moving by walking or by cart between rounds and the user's movement speed is comparatively fast, the display switches from an image displaying the distances to the center and the edge of the green as indicated by the image display region P161 in FIG. 22 to information about a recommended club as indicated by the image display region P162, which is displayed as an interrupt display image. On the other hand, when the user's movement has stopped and the user is assumed to be entering the release, in order to concentrate on the play, the display may be switched from the display of the distances to the center and the edge of the green as indicated by the image display region P163 in FIG. 22 to a state in which nothing is displayed as indicated by the image display region P164, which is displayed as an interrupt display image.

Although the foregoing describes an example of omitting the display of some information to display according to the exercise intensity, the class of sports that the user is currently playing, such as tennis, running, or golf, may be analyzed on the basis of multiple pieces of information included in the exercise intensity, an application corresponding to a sport according to the analysis result may be activated, and a threshold value for configuring whether or not to omit information from display may be set depending on the application program.

In addition, when the exercise intensity is high, information is omitted from display as a general rule, but in cases in which the gaze is directed towards the image display region even for a moment according to gaze detection, information may be displayed without omission.

Furthermore, in cases in which the gaze is directed towards the image display region for a certain amount of time or longer, labels and units may be displayed regardless of the exercise intensity.

In addition, according to the usage frequency of an application, such as if the usage frequency is low, for example, information may be displayed without omission, whereas conversely, if the usage frequency is high, information may be omitted from display.

Third Embodiment

The foregoing describes an example in which the information presented by the images displayed by the display unit 103 is graphics and text, but in some cases, information is displayed in a more easily recognizable manner with images resembling instrument meters or gauges enabling the recognition of approximate degree.

Examples of the display of graphics displayed in an image display region resembling such instrument meters or gauges are illustrated in FIG. 23.

For example, the image display regions G1, G11, and G21 in FIG. 23 illustrate graphics displaying a bar graph depending on the numerical value along the horizontal axis. Herein, the position on the horizontal axis of the apex of the inverted white triangle in the illustrations represents a target value. The case of being lower than the target value (Under) is displayed in the image display region G1, while the case of matching the target value (OK) is displayed in the image display region G11, and the case of being higher than the target value (Over) is displayed in the image display region G21.

Similarly, the image display regions G2, G12, and G22 in FIG. 23 illustrate graphics displaying a bar graph depending on the numerical value along the vertical axis. Herein, the position on the vertical axis of the apex of the inverted white triangle in the illustrations represents a target value. The case of being lower than the target value is displayed in the image display region G2, while the case of matching the target value is displayed in the image display region G12, and the case of being higher than the target value is displayed in the image display region G22.

In addition, the image display regions G3, G13, and G23 in FIG. 23 illustrate graphics displaying a solid-line circle whose radial size with respect to the center position depends on the numerical value. Herein, the distance from the center of the dashed-line circle in the illustrations represents a target value. The case of being lower than the target value is displayed in the image display region G3, while the case of matching the target value is displayed in the image display region G13, and the case of being higher than the target value is displayed in the image display region G23. Note that although an example of expressing the numerical value with the radial size of a true circle is illustrated in FIG. 23, a true circle is not strictly necessary. For example, an ellipse or a square shape made of a polygon may also be used. The outer shape may also be some other freeform shape, insofar as the shape in at least a first direction and a second direction changes depending on the numerical value. In other words, it is sufficient to have a graphic figure made up of a shape which is expressed in a two-dimensional plane and whose respective widths in at least two directions or more can express the magnitude of a numerical value.

Also, the two directions referred to herein are, in the case of the shape being an ellipse, the directions of the major axis and the minor axis, for example. In this case, the major axis and the minor axis are set and the shape is expressed according to the numerical value. Also, the axes in the two directions are orthogonal to each other in the case of an ellipse, but may also be non-orthogonal. Furthermore, the positions at which the major axis and the minor axis are set may also be eccentric. Meanwhile, a true circle is an ellipse for which the major axis and the minor axis are the same.

Furthermore, the image display regions G4, G14, and G24 in FIG. 23 illustrate graphics displaying a bar-shaped needle that rotates with respect to a lower center position by an angle depending on the numerical value. Herein, the position of the inverted white triangle in the illustrations represents a target value. The case of being lower than the target value is displayed in the image display region G4, while the case of matching the target value is displayed in the image display region G14, and the case of being higher than the target value is displayed in the image display region G24.

In addition, the image display regions G5, G15, and G25 in FIG. 23 illustrate graphics displaying an arrow in different directions and a circle depending on the numerical value. Herein, in the case of being lower than the target value, an upward-facing arrow is displayed as indicated by the image display region G5, while in the case of matching the target value, a circle is displayed as indicated by the image display region G15, and in the case of being higher than the target value, a downward-facing arrow is displayed as indicated by the image display region G25.

Furthermore, as indicated by the image display regions G6, G16, and G26 in FIG. 23, the respective specific target value (in the illustrations, displayed as 5 km/h) and current numerical values are displayed as text information. In the image display regions G6, G16, and G26 in FIG. 23, 2 km/h, 5 km/h, and 9 km/h are displayed, respectively.

Regarding these display examples, FIG. 24 illustrates the results of statistically comparing the ease of recognition when still (when not exercising) and the ease of recognition when exercising according to the respective recognition rates.

As a result, the ranking by recognition rate when still becomes the image display regions G4, G2, G1, G3, G5, and G6 from highest to lowest, as indicated in the left part of FIG. 24. However, the ranking by recognition rate when exercising becomes the image display regions G3, G1, G4, G2, G5, and G6 from highest to lowest, as indicated in the right part of FIG. 24.

In other words, the display example with highest recognition rate is the image display region G4 when still, but becomes the image display region G3 when exercising, thereby indicating that there is a difference between the graphics with the highest recognition rate between when still and when exercising.

A possible explanation for this is because, as illustrated in FIG. 25, for the image display region G4 that expresses the numerical value by using an angle, the position pointed to by the tip of the bar indicating the value becomes difficult to see, whereas the image display region G3 that expresses the numerical value by using surface area is easy to recognize even if looking while shaking with respect to the center position.

Given the above, by switching to graphics that are easy to see according to the exercise intensity, namely the movement speed, conceivably it is possible to minimize a reduction in the recognition rate due to exercise.

<Configuration of Third Embodiment of Information Processing Device>

Next, FIG. 26 will be referenced to describe an example configuration of a third embodiment of the information processing device 31, which is configured to switch the graphics for display according to the movement speed. Note that in the information processing device 31 of FIG. 26, components equipped with the same functions as components in the information processing device 31 of FIG. 5 are denoted using the same names and the same signs, respectively, and the description of such components may be reduced or omitted where appropriate.

Namely, the information processing device 31 of FIG. 26 differs from the information processing device 31 of FIG. 5 in that a display control unit 141 is provided instead of the display control unit 102. The basic function of the display control unit 141 is similar to the display control unit 102, but the display control unit 141 varies the graphics used to express information for display according to the movement speed. More specifically, the display control unit 141 is equipped with a mode determination unit 141*a* and a display image generation unit 141*b*. When displaying graphics, the mode determination unit 141*a* switches the display mode among the simultaneous display mode that displays multiple types of information simultaneously, the time-division display mode that display multiple types of information by time division, as well as a high-speed graphics display mode, and a low-speed graphics display mode. The display image generation unit 141*b* basically is equipped with the same function as the display image generation unit 102*b*, but additionally generates and displays on the display unit 103 a display image using graphics in the display mode set by the mode determination unit 141*a*.

Note that the display image generation unit 141*b* generating a display image using graphics means that the display control unit 141 generates display control information for controlling the display unit 103 to display a display image using graphics. Consequently, the display control unit 141 controls the display image generation unit 141*b* to generate display control information and controls the display on the display unit 103 in accordance with the generated display control information, thereby causing a display image using graphics to be displayed on the display unit 103. Also, the display control information referred to herein includes video signal (analog video signal or digital video signal) streaming packets, or instruction information (markup language (Hypertext Markup Language (HTML), Extensible Markup Language (XML))).

Note that in the following, graphics having a high recognition rate at high speeds are simply designated high-speed graphics, and similarly, graphics having a high recognition rate at low speeds are simply designated low-speed graphics.

<Display Control Process by Information Processing Device of FIG. 26>

Next, the flowcharts in FIGS. 27 to 30 will be referenced to describe a display control process by the information processing device 31 of FIG. 26. Note that the processing in steps S81 to S96 and steps S102 to S105 in the flowcharts in FIGS. 27 to 30 is similar to the processing in steps S41 to S56 in FIGS. 16 and 17, and thus description thereof will be reduced or omitted.

In other words, according to the processing from step S81 to S96, if the gaze direction is not fixed and a display is presented while a time t1 or t2 elapses from the previous display time, and if there is no interrupt display, the process proceeds to step S97.

In step S97 (FIG. 28), the mode determination unit 141*a* determines whether or not the user's current movement speed supplied by the activity state information acquisition unit 101 is faster than a certain speed v2, and if not faster, the process proceeds to step S98.

In step S98, the mode determination unit 141*a* switches the display mode setting from the time-division display mode to the low-speed graphics display mode, and supplies the display mode setting to the display image generation unit 141*b*.

In step S99, the mode determination unit 141*a* determines whether or not, in the display image displayed immediately previously, a display image using graphics with a high recognition rate when the movement speed is fast is being displayed. At this point, in the immediately previous display, for example, if the image display regions G3, G13, and G23 in FIG. 23 were used as the graphics with a high recognition rate when the movement speed is fast, for example, high-speed graphics are being displayed, and thus the process proceeds to step S100.

In step S100, the display image generation unit 141*b* varies the display to make a visually recognizable change from high-speed graphics to low-speed graphics in the image being displayed. In other words, the display control unit 141 varies the display to make the process of changing from the graphics that were displayed according to any of the image display regions G3, G13, and G23 in FIG. 23, for example, to graphics with a high recognition rate at low speeds, such as the corresponding graphics of the image display regions G4, G14, and G24, for example, visually recognizable.

More specifically, display images in which the shapes of the graphics displayed in the image display regions G3, G13, and G23 gradually change, such as by animated moving images, for example, are generated and displayed on the display unit 103, thereby causing the display unit 103 to display the shapes changing. The reason for varying the display to make the change visually recognizable in this way is because it is desirable to present the same information with completely different graphics, and thus if the graphics changed suddenly, there is a risk of the user becoming confused as to what information is being presented. Consequently, the graphics before and after the change may be enclosed by the same column or the like to explicitly express that the graphics have changed, for example.

In step S101, the display image generation unit 141*b* causes the display unit 103 to display the nth display information based on the current activity state information using the changed low-speed graphics.

Note that in step S99, if high-speed graphics are not being used, or if low-speed graphics are already being used, the processing in step S100 is skipped, and the nth display information based on the current activity state information is displayed using low-speed graphics.

On the other hand, in step S97, in the case of determining that the movement speed is fast, the process proceeds to step S106.

In step S106, the mode determination unit 141*a* switches the display mode setting from the time-division display mode to the high-speed graphics display mode, and supplies the display mode setting to the display image generation unit 141*b*.

In step S107, the mode determination unit 141*a* determines whether or not, in the display image displayed immediately previously, a display image using graphics with a high recognition rate when the movement speed is slow is being displayed. At this point, in the immediately previous display, for example, if the image display regions G4, G14, and G24 in FIG. 23 were used as the graphics with a high recognition rate when the movement speed is slow, for example, low-speed graphics are being displayed, and thus the process proceeds to step S101.

In step S108, the display image generation unit 141*b* varies the display to make a visually recognizable change from low-speed graphics to high-speed graphics in the image being displayed. In other words, the display control unit 141 causes the display unit 103 to vary the display to make the process of changing from the graphics that were displayed according to any of the image display regions G4, G14, and G24 in FIG. 23, for example, to graphics with a high recognition rate at high speeds, such as the corresponding graphics of the image display regions G3, G13, and G23, for example, visually recognizable.

In step S109, the display image generation unit 141*b* causes the display unit 103 to display the nth display information based on the current activity state information using the changed high-speed graphics.

Note that in step S107, if low-speed graphics are not being used, or if high-speed graphics are already being used, the processing in step S108 is skipped, and the nth display information based on the current activity state information is displayed using high-speed graphics.

In step S96, if interrupt display information is determined to exist, the process proceeds to step S110.

In step S110 (FIG. 29), the mode determination unit 141*a* determines whether or not the user's current movement speed supplied by the activity state information acquisition unit 101 is faster than a certain speed v2, and if not faster, the process proceeds to step S111.

In step S111, the mode determination unit 141*a* switches the display mode setting from the time-division display mode to the low-speed graphics display mode, and supplies the display mode setting to the display image generation unit 141*b*.

In step S112, the display image generation unit 141*b* determines whether or not, in the display image displayed immediately previously, a display image using graphics with a high recognition rate when the movement speed is fast is being displayed. In step S112, if a display image is being displayed using high-speed graphics, the process proceeds to step S113.

In step S113, the display image generation unit 141*b* causes the display unit 103 to vary the display to make a visually recognizable change from high-speed graphics to low-speed graphics in the image being displayed.

In step S114, the display image generation unit 141*b* causes the display unit 103 to display the interrupt display information using the changed low-speed graphics.

Note that in step S112, if high-speed graphics are not being used, or if low-speed graphics are already being used, the processing in step S113 is skipped, and low-speed graphics are used to display the interrupt display information.

On the other hand, in step S110, in the case of determining that the movement speed is fast, the process proceeds to step S115.

In step S115, the mode determination unit 141*a* switches the display mode setting from the time-division display mode to the high-speed graphics display mode, and supplies the display mode setting to the display image generation unit 141*b*.

In step S116, the display image generation unit 141*b* determines whether or not, in the display image displayed immediately previously, a display image using graphics with a high recognition rate when the movement speed is slow is being displayed. In step S116, if a display image is being displayed using low-speed graphics, for example, the process proceeds to step S117.

In step S117, the display image generation unit 141*b* causes the display unit 103 to vary the display to make a visually recognizable change from low-speed graphics to high-speed graphics in the image being displayed.

In step S118, the display image generation unit 141*b* causes the display unit 103 to display the interrupt display information using the changed high-speed graphics.

Note that in step S116, if low-speed graphics are not being used, or if high-speed graphics are already being used, the processing in step S117 is skipped, and high-speed graphics are used to display the interrupt display information.

In step S92 (FIG. 27), in the case of determining that the gaze direction is fixed, the process proceeds to step S119.

In step S119 (FIG. 30), the mode determination unit 141*a* determines whether or not the user's current movement speed supplied by the activity state information acquisition unit 101 is faster than a certain speed v2, and if not faster, the process proceeds to step S120.

In step S120, the mode determination unit 141*a* switches the display mode setting from the time-division display mode to the low-speed graphics display mode, and supplies the display mode setting to the display image generation unit 141*b*.

In step S121, the display image generation unit 141*b* determines whether or not, in the display image displayed immediately previously, a display image using graphics with a high recognition rate when the movement speed is high is being displayed. In step S121, if a display image is being displayed using high-speed graphics, the process proceeds to step S122.

In step S122, the display image generation unit 141*b* causes the display unit 103 to vary the display to make a visually recognizable change from high-speed graphics to low-speed graphics in the image being displayed.

In step S123, the display image generation unit 141*b* causes the display unit 103 to display the display information in the gaze direction using the changed low-speed graphics.

Note that in step S121, if high-speed graphics are not being used, or if low-speed graphics are already being used, the processing in step S122 is skipped, and low-speed graphics are used to display the display information in the gaze direction.

On the other hand, in step S119, in the case of determining that the movement speed is fast, the process proceeds to step S124.

In step S124, the mode determination unit 141*a* switches the display mode setting from the time-division display mode to the high-speed graphics display mode, and supplies the display mode setting to the display image generation unit 141*b*.

In step S125, the display image generation unit 141*b* determines whether or not, in the display image displayed immediately previously, a display image using graphics with a high recognition rate when the movement speed is slow is being displayed. In step S125, if a display image is being displayed using low-speed graphics, for example, the process proceeds to step S126.

In step S126, the display image generation unit 141*b* causes the display unit 103 to vary the display to make a visually recognizable change from low-speed graphics to high-speed graphics in the image being displayed.

In step S127, the display image generation unit 141*b* causes the display unit 103 to display the display information in the gaze direction using the changed high-speed graphics.

Note that in step S125, if low-speed graphics are not being used, or if high-speed graphics are already being used, the processing in step S126 is skipped, and high-speed graphics are used to display the display information in the gaze direction.

According to the above process, it becomes possible to switch to graphics with a high recognition rate for display according to the movement speed, thereby making it possible to minimize a reduction in the recognition rate due to the activity state. In addition, when changing the graphics, the way the shape of the graphics changes is made to be visually recognizable, thereby making it possible to minimize misunderstanding of what kind of information the displayed information is, even when the shape of the graphics changes.

Note that any of the first embodiment to the third embodiment discussed above may also be combined.

Also, the foregoing describes an example in which, as the movement speed becomes faster, the display time of images displayed by being switched successively in a time is lengthened, or in other words, the frame rate is lowered, thereby making text and characters easier to recognize and minimizing a reduction in the recognition rate even while the user is active.

However, in the case of graphics such as the layout G3 in FIG. 23 or the like, it is possible to roughly visualize the approximate degree without reading the detailed position, and thus rather than performing control to lower the frame rate, raising the frame rate to make the shapes expressed by the graphics vary at high speed may possibly allow for expression with a sense of immediacy. Accordingly, for images displayed successively in a time series, depending on the format in which to display information, the display time may be shortened as the movement speed becomes faster, or conversely, the display time may be lengthened as the movement speed becomes faster.

Furthermore, although the foregoing describes an example of displaying a maximum of four different types of information, for the case of displaying more types of information, for example, even if the information is split up and displayed two types at a time, there is a risk of a reduction in the recognition rate due to overlooking the desired information. Accordingly, multiple information types may be split up for display, and in addition, the same information may be repeatedly displayed multiple times. According to such a configuration, if the information can be read at least once out of the multiple times that information is displayed, it becomes possible to minimize overlooking, and as a result, it becomes possible to minimize a reduction in the recognition rate.

In addition, although the foregoing describes an example of controlling the display of images displayed on the display unit 103 by the display control unit 102, 121, or 141 in the information processing device 31, the configuration corresponding to the display control unit 102, 121, or 141 is not required to be built into the information processing device, and may also be provided on the Internet or on a local network, for example, so that only the information of images to be displayed is displayed by the information processing device 31 worn on the eyeglasses 11.

The foregoing describes an example of switching graphics according to the exercise intensity, but graphics may also be switched according to a component in the vibration direction. For example, if the graphics G1 in FIG. 23, for which change in the value is easy to recognize in the horizontal direction, is being used and displayed, when vibration in the horizontal direction is detected, the graphics may be switched to graphics having a vertical component as the axis that expresses the value, such as the graphics G2 or G3 in FIG. 23, for example. Conversely, for example, if the graphics G2 in FIG. 23, for which change in the value is easy to recognize in the vertical direction, is being used and displayed, when vibration in the vertical direction is detected, the graphics may be switched to graphics having a horizontal component as the axis that expresses the value, such as the graphics G1 or G3 in FIG. 23, for example.

Furthermore, the information processing device 31 may also be provided on a network and be configured to control the display unit 103 on the eyeglasses 11 through the network (the Internet, or a local network).

In addition, the first to the third embodiments discussed above may also be configured as follows.

For example, as illustrated in FIG. 31, an HMD 201 equipped with the activity state information acquisition unit 101, the display unit 103, the operating unit 104 the storage unit 105 and the gaze detection unit 106 may be configured as a separate device from the information processing device 31 equipped with any of the display control unit 102, 121, or 141, and the separate devices may be configured to communicate with each other by wired communication, or by wireless communication using a protocol such as Wi-Fi or Bluetooth. In this case, the information processing device 31 is configured as a mobile terminal, such as a smartphone, for example.

Furthermore, as illustrated in FIG. 32, the HMD 201 and the information processing device 31 may also be connected over a network 221, such as the Internet or an intranet. In this case, the information processing device 31 is configured as a server on the network or the like, for example.

<Execution by Software>

Incidentally, the above series of processes can, for example, be executed by hardware, or can be executed by software. In the case where the series of processes is executed by software, a program configuring this software is installed in a computer included in dedicated hardware, or a general-purpose personal computer which can execute various functions when various programs are installed, etc., from a recording medium.

FIG. 33 shows an example configuration of a general-purpose personal computer. The computer includes a CPU (Central Processing Unit) 1001. An input/output interface 1005 is connected to the CPU 1001 through a bus 1004. A ROM (Read Only Memory) 1002 and a RAM (Random Access Memory) 1003 are connected to the bus 1004.

An input unit 1006 including an input device, such as a keyboard, a mouse, etc., which is used by the user to input an operation command, an output unit 1007 which outputs a process operation screen or an image of a process result to a display device, a storage unit 1008 including a hard disk drive etc. which stores a program or various items of data, and a communication unit 1009 including a LAN (Local Area Network) adaptor etc. which performs a communication process through a network typified by the Internet, are connected to the input/output interface 1005. Also, connected is a drive 1010 which reads and writes data from and to a removable medium 1011, such as a magnetic disk (including a flexible disk), an optical disk (including a CD-ROM (Compact Disc-Read Only Memory) and a DVD (Digital Versatile Disc)), an magneto-optical disk (including an MD (Mini Disc)), or a semiconductor memory, etc.

The CPU 1001 executes various processes according to a program stored in the ROM 1002 or a program which is read from the removable medium 1011, such as a magnetic disk, an optical disk, a magneto-optical disk, or a semiconductor memory, etc., is installed in the storage unit 1008, and is loaded from the storage unit 1008 to the RAM 1003. The RAM 1003 also stores data which is necessary when the CPU 1001 executes various processes, etc., as appropriate.

In the computer configured as described above, the CPU 1001 loads a program that is stored, for example, in the storage unit 1008 onto the RAM 1003 via the input/output interface 1005 and the bus 1004, and executes the program. Thus, the above-described series of processing is performed.

Programs to be executed by the computer (the CPU 1001) are provided being recorded in the removable medium 1011 which is a packaged medium or the like. Also, programs may be provided via a wired or wireless transmission medium, such as a local area network, the Internet or digital satellite broadcasting.

In the computer, by inserting the removable medium 1011 into the drive 1010, the program can be installed in the storage unit 1008 via the input/output interface 1005. Further, the program can be received by the communication unit 1009 via a wired or wireless transmission medium and installed in the storage unit 1008. Moreover, the program can be installed in advance in the ROM 1002 or the storage unit 1008.

It should be noted that the program executed by a computer may be a program that is processed in time series according to the sequence described in this specification or a program that is processed in parallel or at necessary timing such as upon calling.

Further, in the present disclosure, a system has the meaning of a set of a plurality of configured elements (such as an apparatus or a module (part)), and does not take into account whether or not all the configured elements are in the same casing. Therefore, the system may be either a plurality of apparatuses, stored in separate casings and connected through a network, or a plurality of modules within a single casing.

An embodiment of the disclosure is not limited to the embodiments described above, and various changes and modifications may be made without departing from the scope of the disclosure.

For example, the present disclosure can adopt a configuration of cloud computing which processes by allocating and connecting one function by a plurality of apparatuses through a network.

Further, each step described by the above-mentioned flow charts can be executed by one apparatus or by allocating a plurality of apparatuses.

In addition, in the case where a plurality of processes are included in one step, the plurality of processes included in this one step can be executed by one apparatus or by sharing a plurality of apparatuses.

Additionally, the present technology may also be configured as below.

<1> An information processing device including:

an activity state information acquisition unit configured to acquire activity state information; and a display mode setting unit configured to set a display mode from among a plurality of display modes on the basis of the activity state information acquired by the activity state information acquisition unit, in which the plurality of display modes includes a first display mode of simultaneously displaying first information and second information different from the first information, and a second display mode of displaying the first information and the second information at different timing.

<2> The information processing device according to <1>, in which the plurality of display modes includes the first display mode of simultaneously displaying the first information and the second information, and the second display mode of displaying the first information and the second information at different timing in separate time periods.

<3> The information processing device according to <2>, in which the display mode setting unit sets the first display mode of simultaneously displaying the first information and the second information, and the second display mode of displaying the first information at first timing and displaying the second information at second timing different from the first timing.

<4> The information processing device according to <2>, in which the plurality of display modes includes the first display mode of simultaneously displaying the first information and the second information, and a second display mode of displaying the first information at first timing and displaying the second information at second timing different from the first timing, the first timing and the second timing not being overlapped with each other.

<5> The information processing device according to <4>, in which the display mode setting unit sets a simultaneous display mode of simultaneously displaying the first information and the second information, and a time-division display mode of displaying the first information at first timing and displaying the second information at second timing different from the first timing by time division.

<6> The information processing device according to any one of <1> to <5>, in which the activity state information includes user's exercise intensity.

<7> The information processing device according to <6>, in which the user's exercise intensity is specified by measurement of movement speed, vibration, gaze, heart rate, body temperature, perspiration, brain waves, or myoelectric potential of the user.

<8> The information processing device according to <1>, in which the display mode setting unit sets the first display mode of simultaneously displaying the first information and the second information in a case where the exercise intensity is weaker than a first certain threshold value, and sets the second display mode of displaying the first information and the second information at different timing in separate time periods in a case where the exercise intensity is stronger than the first certain threshold value.

<9> The information processing device according to <8>, in which the display mode setting unit sets display time, during which the first information and the second information are displayed, according to the exercise intensity in a case where the exercise intensity is stronger than the first certain threshold value and the second display mode of displaying the first information and the second information at different timing in separate time periods is set.

<10> The information processing device according to <8>, in which in a case where the exercise intensity is stronger than the first certain threshold value and the second display mode of displaying the first information and the second information at different timing in separate time periods is set, the display mode setting unit sets that the certain number of pieces of information are displayed each for first display time if the exercise intensity is weaker than a second certain threshold value larger than the first certain threshold value, and sets that the first information and the second information are displayed for second display time if the exercise intensity is stronger than the second certain threshold value.

<11> The information processing device according to any one of <1> to <10>, in which the first display time is shorter than the second display time.

<12> The information processing device according to <10>, in which the first display time is longer than the second display time.

<13> The information processing device according to <6>, in which in a case where the exercise intensity is stronger than the first certain threshold value and the second display mode of displaying the first information and the second information at different timing in separate time periods is set, the display mode setting unit sets that the certain number of pieces of information are displayed each for first display time if the exercise intensity is weaker than a second certain threshold value larger than the first certain threshold value, and sets that the first information and the second information are displayed for second display time if the exercise intensity is stronger than the second certain threshold value larger than the first certain threshold value.

<14> The information processing device according to any one of <1> to <13>, in which the display mode setting unit sets display time, during which the first information and the second information are displayed, according to importance of information to be displayed.

<15> The information processing device according to any one of <1> to <14>, in which the plurality of display modes includes the first display mode of simultaneously displaying the first information and the second information, and the second display mode of displaying the first information and the second information at different timing according to exercise intensity on the basis of user's operation contents.

<16> The information processing device according to any one of <1> to <15>, further including a display image generation unit configured to generate an image according to the display mode set by the display mode setting unit.

<17> The information processing device according to <16>, further including a display unit configured to display an image which can be seen along with an outside world, in which the display unit displays, as the display image, the image generated by the display image generation unit according to the display mode set by the display mode setting unit.

<18> The information processing device according to any one of <1> to <17>, in which the display unit further includes displaying of the display image displayed by an eyepiece optical system in which a length in a direction, which is shorter than the other directions, of a region where light is emitted towards user's pupil is shorter than or equal to an upper limit of pupil diameter variation.

<19> The information processing device according to any one of <1> to <18>, in which the display mode setting unit controls displaying of a mobile terminal.

<20> An information processing method including the steps of:

acquiring activity state information; and setting a display mode from among a plurality of display modes on the basis of the acquired activity state information, in which the plurality of display modes includes a first display mode of simultaneously displaying first information and second information different from the first information, and a second display mode of displaying the first information and the second information at different timing.

<21> A program causing a computer to function as:

an activity state information acquisition unit configured to acquire activity state information; and a display mode setting unit configured to set a display mode from among a plurality of display modes on the basis of the activity state information acquired by the activity state information acquisition unit, in which the plurality of display modes includes a first display mode of simultaneously displaying first information and second information different from the first information, and a second display mode of displaying the first information and the second information at different timing.

REFERENCE SIGNS LIST 11 eyeglasses
31 information processing device
41 main unit
41a operating unit
42 arm
43 light guide reflection unit
51 light guide unit
61 eyepiece lens
71 projection unit
72 reflection unit
101 activity state information acquisition unit
102 display control unit
102a display control unit
102b display image generation unit
103 display unit
104 operating unit
105 storage unit
106 gaze detection unit
121 display control unit
121a mode determination unit
121b display image generation unit
141 display control unit
141a mode determination unit
141b display image generation unit

The invention claimed is:

1. An information processing device comprising:

an activity state information acquisition unit configured to acquire activity state information, wherein the activity state information includes a user's exercise intensity; and a display mode setting unit configured to set a display mode from among a plurality of display modes on the basis of the activity state information acquired by the activity state information acquisition unit, wherein the plurality of display modes includes a first display mode of simultaneously displaying first information and second information different from the first information, and a second display mode of displaying the first information and the second information at different timing, wherein the display mode setting unit sets the first display mode of simultaneously displaying the first information and the second information in a case where the exercise intensity is weaker than a first threshold value, and sets the second display mode of displaying the first information and the second information at different timing in a case where the exercise intensity is stronger than the first threshold value, wherein, in a case where the second display mode of displaying the first information and the second information at different timing is set, the display mode setting unit sets a display switching time during which the first information is displayed and switched to the second information, wherein the display switching time is set based on the activity state information, wherein the display switching time is set to a first time based on the user's exercise intensity being a first level, and the display switching time is set to a second time longer than the first time based on the user's exercise intensity being a second level stronger than the first level, and wherein the activity state information acquisition unit and the display mode setting unit are each implemented via at least one processor.

2. The information processing device according to claim 1, wherein the plurality of display modes includes the first display mode of simultaneously displaying the first information and the second information, and the second display mode of displaying the first information and the second information at different timing in separate time periods.

3. The information processing device according to claim 2, wherein the plurality of display modes includes the first display mode of simultaneously displaying the first information and the second information, and the second display mode of displaying the first information at first timing and displaying the second information at second timing different from the first timing, the first timing and the second timing not being overlapped with each other.

4. The information processing device according to claim 1, wherein the user's exercise intensity is specified by movement speed, measurement of vibration, gaze, heart rate, body temperature, perspiration, brain waves, or myoelectric potential of the user.

5. The information processing device according to claim 4, wherein the display mode setting unit sets the first display mode when the movement speed is less than or equal to a threshold speed and sets the second display mode when the movement speed is greater than the threshold speed.

6. The information processing device according to claim 1, wherein, in a case where the exercise intensity is stronger than the first threshold value and the second display mode of displaying the first information and the second information at different timing in separate time periods is set, the display mode setting unit sets a length of display time, during which the first information and the second information are displayed, according to the exercise intensity.

7. The information processing device according to claim 1, wherein in a case where the exercise intensity is stronger than the first threshold value and the second display mode of displaying the first information and the second information at different timing in separate time periods is set, the display mode setting unit sets that a number of pieces of information are displayed each for first display time if the exercise intensity is weaker than a second threshold value larger than the first threshold value, and sets that the first information and the second information are displayed for second display time if the exercise intensity is stronger than the second threshold value.

8. The information processing device according to claim 7, wherein the first display time is shorter than the second display time.

9. The information processing device according to claim 7, wherein the first display time is longer than the second display time.

10. The information processing device according to claim 1, wherein in a case where the exercise intensity is stronger than the first threshold value and the second display mode of displaying the first information and the second information at different timing in separate time periods is set, the display mode setting unit sets that a number of pieces of information are displayed each for first display time if the exercise intensity is weaker than a second threshold value larger than the first threshold value, and sets that the first information and the second information are displayed for second display time if the exercise intensity is stronger than the second threshold value larger than the first threshold value.

11. The information processing device according to claim 1, wherein the display mode setting unit sets a length of display time, during which the first information and the second information are displayed, according to importance of information to be displayed.

12. The information processing device according to claim 1, wherein the plurality of display modes includes the first display mode of simultaneously displaying the first information and the second information, and the second display mode of displaying the first information and the second information at different timing according to exercise intensity on the basis of the user's operation contents.

13. The information processing device according to claim 1, further comprising:

a display image generation unit configured to generate an image according to the display mode set by the display mode setting unit, wherein the display image generation unit is implemented via at least one processor.

14. The information processing device according to claim 13, further comprising:

a display unit configured to display a display image which can be seen along with an outside world, wherein the display unit displays, as the display image, the image generated by the display image generation unit according to the display mode set by the display mode setting unit.

15. The information processing device according to claim 14, wherein the display unit further includes displaying of the display image displayed by an eyepiece optical system in which a length in a direction, which is shorter than other directions, of a region where light is emitted towards user's pupil is shorter than or equal to an upper limit of pupil diameter variation.

16. The information processing device according to claim 1, wherein the display mode setting unit controls displaying of a mobile terminal.

17. The information processing device according to claim 1, wherein, in the case where the second display mode of displaying the first information and the second information at different timing is set, the display mode setting unit sets the display switching time during which the first information is displayed and the second information is not displayed and switched to the second information being displayed and the first information not being displayed.

18. An information processing method comprising:

acquiring activity state information;

setting a display mode from among a plurality of display modes on the basis of the acquired activity state information, wherein the activity state information includes a user's exercise intensity, wherein the plurality of display modes includes a first display mode of simultaneously displaying first information and second information different from the first information, and a second display mode of displaying the first information and the second information at different timing;

setting, in a case where the exercise intensity is weaker than a first threshold value, the first display mode of simultaneously displaying the first information and the second information;

setting, in a case where the exercise intensity is stronger than the first threshold value, the second display mode of displaying the first information and the second information at different timing, and setting, in a case where the second display mode of displaying the first information and the second information at different timing is set, a display switching time during which the first information is displayed and switched to the second information;

wherein the display switching time is set based on the activity state information, and wherein the display switching time is set to a first time based on the user's exercise intensity being a first level, and the display switching time is set to a second time longer than the first time based on the user's exercise intensity being a second level stronger than the first level.

19. A non-transitory computer-readable storage medium having embodied thereon a program, which when executed by a computer causes the computer to execute a method, the method comprising:

acquiring activity state information, wherein the activity state information includes a user's exercise intensity;

setting a display mode from among a plurality of display modes on the basis of the acquired activity state information, wherein the plurality of display modes includes a first display mode of simultaneously displaying first information and second information different from the first information, and a second display mode of displaying the first information and the second information at different timing;

setting, in a case where the exercise intensity is weaker than a first threshold value, the first display mode of simultaneously displaying the first information and the second information;

setting, in a case where the exercise intensity is stronger than the first threshold value, the second display mode of displaying the first information and the second information at different timing, and setting, in a case where the second display mode of displaying the first information and the second information at different timing is set, a display switching time during which the first information is displayed and switched to the second information;

wherein the display switching time is set based on the activity state information, and wherein the display switching time is set to a first time based on the user's exercise intensity being a first level, and the display switching time is set to a second time longer than the first time based on the user's exercise intensity being a second level stronger than the first level.

* * * * *